US009851347B2

(12) United States Patent
Cottier

(10) Patent No.: US 9,851,347 B2
(45) Date of Patent: Dec. 26, 2017

(54) FLOW CONDUIT SYSTEM FOR A BIOCHEMICAL SENSOR

(71) Applicant: Creoptix Ltd., Wadenswil (CH)

(72) Inventor: Kaspar Cottier, Wadenswil (CH)

(73) Assignee: Creoptix AG (CH)

( * ) Notice: Subject to any disclaimer, the term of this patent is extended or adjusted under 35 U.S.C. 154(b) by 270 days.

(21) Appl. No.: 14/403,845

(22) PCT Filed: Jul. 5, 2013

(86) PCT No.: PCT/EP2013/064290
§ 371 (c)(1),
(2) Date: Nov. 25, 2014

(87) PCT Pub. No.: WO2014/009286
PCT Pub. Date: Jan. 16, 2014

(65) Prior Publication Data
US 2015/0192574 A1    Jul. 9, 2015

(30) Foreign Application Priority Data

Jul. 7, 2012 (CH) ........................................ 1053/12

(51) Int. Cl.
*G01N 33/53* (2006.01)
*G01N 35/08* (2006.01)
(52) U.S. Cl.
CPC ....... *G01N 33/5302* (2013.01); *G01N 35/085* (2013.01)
(58) Field of Classification Search
CPC .......................... G01N 35/1095; G01N 35/085
See application file for complete search history.

(56) References Cited

U.S. PATENT DOCUMENTS

| 6,008,893 | A | 12/1999 | Roos et al. |
| 2005/0019933 | A1* | 1/2005 | Andersson ........... G01N 35/085 436/52 |
| 2006/0234209 | A1* | 10/2006 | Walker ................. G01N 33/537 435/5 |

(Continued)

FOREIGN PATENT DOCUMENTS

| EP | 0345782 A2 | 12/1989 |
| JP | 2005017057 A | 1/2005 |

(Continued)

*Primary Examiner* — P. Kathryn Wright
(74) *Attorney, Agent, or Firm* — Blank Rome LLP

(57) ABSTRACT

A flow conduit system (100, 200a, 200b) suitable for biochemical sensing, the flow conduit system (100, 200a, 200b) having a first flow cell conduit (1) with one or more sensing areas for biochemical sensing; a first selector valve (4); a first inlet/outlet conduit (2) which fluidly connects the first flow cell conduit (1) to the first selector valve (4); a first injection conduit (6) having a first end and a second end; a second injection conduit (7) having a first end and a second end; a fluid injecting means (8) fluidly connected to the second ends of each of the first and second injection conduits (6, 7) so that the fluid injecting means can selectively inject fluids into the first and/or second injection conduits (6,7); wherein the first injection conduit (6) is fluidly connected, at its first end, to the first inlet/outlet conduit (2) by a valveless junction (9), and the second injection conduits (6) is fluidly connected, at its first end, to the first inlet/outlet conduit (2) by a valveless junction (9).

14 Claims, 4 Drawing Sheets

(56) References Cited

U.S. PATENT DOCUMENTS

2009/0130766 A1 5/2009 Weekamp
2009/0142846 A1 6/2009 Crenshaw et al.

FOREIGN PATENT DOCUMENTS

| WO | WO-9930349 A1 | 6/1999 |
| WO | WO-200057192 A2 | 9/2000 |
| WO | WO-200122068 A1 | 3/2001 |
| WO | WO-200236485 A1 | 5/2002 |
| WO | WO-2003069317 A | 8/2003 |
| WO | WO-2004109284 A1 | 12/2004 |
| WO | WO-2008110026 A1 | 9/2008 |
| WO | WO-2009014553 A1 | 1/2009 |

* cited by examiner

FLOW CONDUIT SYSTEM FOR A BIOCHEMICAL SENSOR

REFERENCE DATA

The present application is a national stage of PCT/EP2013/064290, filed Jul. 5, 2013, which claims priority of the Swiss patent application CH1053/12 filed Jul. 7, 2012. The content of those applications are hereby incorporated by reference.

The invention is related to the field of label-free optical sensors with high sensitivity, large measuring range, high readout speed, simple device handling, low maintenance requirements and high robustness with respect to manufacturing tolerances, particularly consisting of integrated-optical waveguides, flow chambers and a readout device, and their application to (bio-) chemical sensor units, as they find use, for example, in pharmacology or in diagnostics.

DESCRIPTION OF RELATED ART

Sensing devices for the measurement of molecular interactions (biochemical sensors) can be split into two categories; namely label-free sensors and sensors which operate using a marker. These sensors are generally known in the field of life sciences, and are mainly used for the characterization of interactions of biologic or biochemical molecules. These characterizations commonly involve bringing two or more different types of sample molecules into physical contact with each other for a set period of time and then measuring if, for example, the sample molecules have bound to form a molecular complex. The kinetics (speed) and affinity (strength) of these molecular bindings are the two main parameters often measured during these characterization procedures.

Biochemical sensors are also used for other applications such as molecular detection or concentration determination, by making use of a selective high affinity binding between two molecules. The main application of biochemical sensors lies in the field of drug discovery, e.g., in the selection of drug candidates by measuring the binding affinity and kinetics between a potential drug and a drug target Important applications involving molecular detection or concentration determination lie in the field of diagnostics, for example, in blood or urine tests, the search for pathogens, or in the analysis of allergies. Other applications are, for example, in fields such as process control, food, or environmental.

Sensing methods using a marker operate by chemically attaching a marker, typically a fluorescent, absorbing or radioactive molecule to a target molecule which is to be detected. Here, the presence and concentration of the target molecule is the determined indirectly by measuring the presence and concentration of the marker. While marker-based methods are widely used throughout the field of life sciences, they have the main disadvantages that the marker can alter the binding affinity or kinetics of the target molecule, and that the attachment of the marker can be time consuming.

Compared to marker-based methods, label-free sensing methods operate without attaching any marker to the target molecule, but measure directly the presence of a target molecule. They therefore have the advantage that the binding of the target molecule is not influenced by the presence of a marker. This is important for example in the field of drug discovery for the observation of the binding of small active molecules to a corresponding drug target (such as Aspirin to the COX-2 Enzyme), since the binding characteristics of small target molecules would be readily disturbed by a marker attached to it. Another advantage lies in the potential reduction of costs and time necessary for a measurement, since the marker attachment step is omitted. Amongst others, the requirements for a sensing method without markers are: high sensitivity, so that also tiny amounts of target molecules, the smallest interactions, or the smallest target molecules can be sensed; a high readout speed, so that a fast (bio-) chemical binding or reaction can be traced with the necessary resolution; the possibility of a massively parallel readout of many measurement areas or subunits of a sensor platform, the latter mainly in the format of micro titer plates which are used in the pharmaceutical industry for high throughput screening (HTS), permitting a parallel readout of up to several hundred or even thousand processes; a large measurement range, so that different processes with different signal amplitudes can be sensed at the same time; low cost per measurement point; simple device handling and user interfaces; and low maintenance costs.

Methods for label-free sensing include, but are not limited to, optical methods based on surface plasmon resonance (SPR) or waveguides, or methods based on surface-acoustic waves (SAW), thermal methods, or electro-chemical methods. Optical methods are based on the principle that biochemical molecules show a different refractive index than an aqueous solution. Refractive index changes on the sensor surface result from the addition or subtraction of molecules onto the surfaces due to the interaction of molecules with either the sensor surface itself or another molecule attached to the surface. Using a resonant element—in case of SPR a metal layer supporting surface plasmons, or in case of waveguide sensors an optical waveguide supporting optical waveguide modes—the local refractive index changes can be then probed using an appropriate illumination and detection scheme, and the changes recorded in real time in order to sense the molecular binding event. In this context, these changes correspond to the sensor signal. Surface-Acoustic Wave and electro-chemical methods operate in a similar way, except that not the refractive index differences are physically measured, but rather mass or permittivity differences.

In this context, many label-free sensing techniques or label-free measurements or label-free assays involve attaching (immobilizing) of one or more "ligands" (such as an antibodies or drug targets) to a solid support on a sensing surface (i.e. a sensitized surface on a sensor chip which is adapted to be read out by a detection scheme which outputs the sensor signal). The fluid conduit containing the sensing surface is generally called flow cell or fluidic chamber and allows bringing a fluid containing the other molecule(s) to be investigated (analyte) to be brought into contact with the ligand. Thereby molecule(s) to be investigated (analyte) have the opportunity to interact with the immobilized ligands at the solid support on a sensing surface and an eventual binding measured and characterized. Typically, the characterization is performed as kinetic affinity measurement, wherein the binding (association) and separation (dissociation) phases of molecular interactions between the ligands and molecule(s) to be investigated (analyte) are monitored in order to extract the kinetic association and dissociation rates, which relate to the concentration-dependent time constants characterizing the binding. A typical kinetic measurement procedure consists in first contacting the surface-bound ligand first with a neutral buffer solution in order to establish a base sensor signal without binding ("baseline"), followed by contacting the surface-bound ligand with a fluid containing the actual analyte or sample (such as an antigen) so that the surface-bound ligand binds with the analyte or sample, and the association phase of the binding reaction can be monitored, and optionally followed by contacting the surface-bound ligand again with a neutral buffer solution in order to monitor the dissociation phase of the analyte or sample by removing the analyte from the flow cell. In other words, the concentration of the analyte is increased in a step-wise fashion for characterizing the association phase, and decreased again in a step-wise fashion for characterizing the dissociation phase.

Typically, during the whole time of the measurement, the sensor signal is recorded, resulting in sensor signal curves or sensors grams, which may be further analyzed, typically by fitting a model to the sensor signal curves.

It is intuitively understood that a quick reaction between the ligand and the analyte cannot be monitored if the concentration of the analyte is increasing slower than the time constant of the binding reaction itself. Therefore, an important requirement for label-free devices for kinetic affinity measurements is a rapid fluid transition or fluid exchange at the sensor (i.e. within the flow cell), such as the buffer solution and the analyte sample, so that the concentration increase and decrease occurs much faster than the time constants of the binding reactions to be observed. This is important for measuring fast kinetic reactions between the sample and the surface bound molecules without being limited by the time constants of the fluidic system. In other words, the concentration of the fluid containing the analyte at the sensor should, at a given moment, increase from 0% to 100% in a minimal amount of time (often referred to as transition time). It is also necessary that there is no significant mixing between the buffer solution and the fluid containing the analyte or sample, in other words that the analyte or sample is not diluted, since then the sample or analyte concentration within the flow cell would not correspond to the initial sample or analyte concentration. Since this concentration is in general an important parameter in the analysis, the results of the analysis would be falsified by this dilution. Furthermore, the fluid containing the analyte or sample, should not contact the sensing surface of the sensor prior to a measurement, since part of the sensing surface could get pre-loaded with the analyte or sample, and such a pre-loading typically alters the determined kinetic rates (by providing a different initial condition since a part of the binding reaction occurs prior to the actual measurement) and total amount of molecular deposition during the actual measurement.

WO0236485 describes a valve system for a biosensor based on surface plasmon resonance (SPR). The system utilized microvalves integrated in a fixed liquid handling block close to the sensor surface in order to achieve the fast switchover-time between fluids. A major disadvantage of the system is that the microfluidic system is complicated and thus expensive, mainly due to the integration of the microfluidic valves. Also, the conduits and valves inside the fluidic block can be subject to clogging and cannot be exchanged easily. Furthermore, the delicate sensor surface is exposed prior to chip insertion and is not protected against dust deposition or accidental touching.

WO0057192 describes a reversible flow system for a biosensor, where no integrated valves in proximity of the flow cell are needed. However, in this system the dead volumes between the valves and the flow cell become important obstacles to clean and rapid fluid transitions between a first fluid, such as a buffer solution, and a second fluid, such as the sample solution. Furthermore, the flow directions of the two flows are not identical, which is an obstacle to the analysis of experimental results, since the flow parameters for buffer and sample solution should match as closely as possible especially for high sensitivity measurements where sensing and reference surfaces are connected in series. Also, the fluid system with conduits of small cross-section can not be exchanged easily since it is an integral part of the instrument, and the delicate chip sensing surface is not protected.

WO 03/069317 and EP 1 214 580 describe interferometric sensor systems which are highly sensitive to misalignment, thus requiring considerable effort for aligning the optical waveguide with respect to incident light and output detectors. Also, great efforts with respect to accurate temperature control and precise positioning of microfluidic chambers are needed in order not to deteriorate the sensor signal. Furthermore, in this system the dead volumes between the valves and the flow cell become important obstacles to clean and rapid fluid transitions between a first fluid, such as a buffer solution, and a second fluid, such as the sample solution.

WO 2008110026 describes a sensor with high sensitivity, large measuring range, high readout speed, and high robustness with respect to manufacturing tolerances. In contrast to conventional biochemical sensors based on SPR or waveguide transducers, the sensor is very tolerant to misalignment both in position and angle.

BRIEF SUMMARY OF THE INVENTION

It is therefore the objective of the invention to create a sensor device which can be used in particular for (bio-)chemical measurements of the type mentioned at the outset, which provides fast fluid transitions, a high sensitivity, a large measuring range, a high readout speed, low costs per measuring point, simple device handling, low maintenance requirements and high robustness with respect to manufacturing tolerances.

This task is performed by a flow conduit system and associated biochemical sensor device, as well as an associated cartridge, and a method to operate said sensor device, using the properties of the corresponding, independent patent claims.

Traditionally, as mentioned in WO0057192, fast fluid transitions can only be achieved by minimizing the volume between the flow cell and the active switching valves which control the fluid exchange in the flow cell (sensor). In this context, this volume is often referred to as "dead volume". Upon switching from neutral buffer solution to the sample or analyte to be measured, this sample fluid first needs to travel through the dead volume which is filled by the neutral buffer solution. During that time, mixing between the sample fluid and the neutral buffer fluid occurs, resulting in a concentration gradient at the flow cell until the dead volume is completely "rinsed" by the sample fluid. Therefore, the fluid transition or switching time is related to the dead volume. As a rule of thumb and for typical channel geometries with widths, depths or diameters of 10 μm to a few millimeters, the transition time amounts to three to five times the dead volume divided by the volumetric flow rate. However, placing the switching valves close to the flow cell (sensor) is costly and may create artifacts in the sensor signal, originating from mechanical movements and vibrations transmitted from the valves to the sensing areas of the flow cell. Typically, these artifacts comprise sudden spikes or fluctuations in the sensor signal readout. Surprisingly, fast fluid transitions can be achieved with the current invention even with a significant volume between active valves and the flow cell, therefore eliminating the unwanted higher costs and parasitic effects.

In this context, a flow conduit can be, but is not limited to, a microfluidic channel or a tube.

According to the invention, the flow conduit system comprises a first flow cell conduit with a first inlet/outlet conduit at a first end, and a second inlet/outlet conduit at a second end. The first flow cell conduit comprises sensing areas to be contacted by typically at least two different fluids. Therefore according to the present invention there is provided a flow conduit system suitable for biochemical sensing, the flow conduit system comprising, a first flow cell conduit comprising one or more sensing areas for biochemical sensing; a first selector valve; a first inlet/outlet conduit which fluidly connects the first flow cell conduit to the first selector valve; a first injection conduit having a first end and a second end; a second injection conduit having a first end and a second end; a fluid injecting means fluidly connected to the second ends of each of the first and second injection conduits so that the fluid injecting means can selectively inject fluids into the first and/or second injection conduits; wherein the first injection conduit is fluidly connected, at its first end, to the first inlet/outlet conduit by a valveless junction, and the second injection conduits is fluidly connected, at its first end, to the first inlet/outlet conduit by a valveless junction.

Because the first and second injection conduits are each fluidly connected to the first inlet/outlet conduit by a valveless junction, there are no valves located on a fluid path between the injecting means the first flow cell conduit. Accordingly there is no valves located close to the first flow cell conduit which could affect the performance of the first flow cell conduit when biochemical sensing.

The first injection conduit may be fluidly connected, at its first end, to the first inlet/outlet conduit by a first valveless junction, and the second injection conduit may be fluidly connected, at its first end, to the first inlet/outlet conduit by a second valveless junction so that fluid path between the fluid injecting means. In this case it is preferable that the valveless junction is a three-way junction e.g. is a Y-shaped junction or a T-shaped junction.

Alternatively the first injection conduit may be fluidly connected, at its first end, to the first inlet/outlet conduit by a valveless junction, and the second injection conduits may be fluidly connected, at its first end, to the first inlet/outlet conduit by the the same valveless junction so that fluid path between the fluid injecting means. In this case a single valveless junction is provided which is preferably a four-way junction. Preferably the first injection conduit and the second injection conduit are each valveless. Preferably the portion of the first inlet/outlet conduit which is between the first flow cell conduit and the or each valveless junction is valveless. Preferably the portion of the first inlet/outlet conduit which is between the first flow cell conduit and the first valveless junction is valveless. Preferably the portion of the first inlet/outlet conduit which is between the first flow cell conduit and the second valveless junction is valveless.

Preferably the fluid injecting means is valveless.

The fluid injecting means preferably comprises a means by which the volume of fluid which is injected from the fluid injecting means into the first and/or second injection conduits can be controlled.

The fluid injecting means preferably comprises a means by which the rate at which fluid is injected from the fluid injecting means into the first and/or second injection conduits can be controlled.

The fluid injecting means may comprise one or more syringe pumps. Syringe pumps comprise a piston which moves inside a cylinder; the piston provides the means by which the volume of fluid and the rate at which fluid is injected from the fluid injecting means into the first and/or second injection conduits. The amount and speed the piston is moved inside the cylinder determines, respectively, the volume of fluid and the rate at which the fluid is injected. However, it will be understood that there are many other fluid injecting means which could be used which comprise other means for controlling the volume and rate at which the fluid is injected from the fluid injecting means into the first and/or second injection conduits.

The volume of the first inlet/outlet conduit which is between the first flow cell conduit and the or each valveless junction is preferably less than 10 microliters.

The volume of the first inlet/outlet conduit which is between the first flow cell conduit and at least one of the first or second valveless junctions is preferably less than 10 microliters.

The volume of the first inlet/outlet conduit which is between the first flow cell conduit and the or each valveless junction is preferably less than 1 microliters.

The volume of the first inlet/outlet conduit which is between the first flow cell conduit and at least one of the first or second valveless junctions is preferably less than 1 microliters.

Preferably the volume of the first inlet/outlet conduit which is between the first flow cell conduit and both of the first and second valveless junctions is less than 10 microliters.

Preferably the volume of the first inlet/outlet conduit which is between the first flow cell conduit and both of the first or second valveless junctions is less than 1 microliters.

The flow conduit system further may comprise a second inlet/outlet conduit fluidly connected to the first flow cell conduit; a second selector valve, wherein the second inlet/outlet conduit fluidly connects the first flow cell conduit to the second selector valve.

Preferably the first inlet/outlet conduit is connected to a first end of the first flow cell conduit and the second inlet/outlet conduit is connected to a second end of the first flow cell conduit such that fluid can flow from the first inlet/outlet conduit through the flow cell conduit and into the second inlet/outlet conduit, and vice versa.

The first selector valve may be further fluidly connected to a receptacle which can hold fluids.

The second selector valve may be further fluidly connected to a receptacle which can hold fluids.

The flow conduit system further comprise a control unit for controlling the fluid injection means such that the volume of fluid which is injected from the fluid injecting means into the first and/or second injection conduits, and the rate at which fluid is injected from the fluid injecting means into the first and/or second injection conduits, is automatically controlled.

Preferably the control unit is further configured to control the first selector valve.

Preferably the control unit is further configured to control the first and/or second selector valves.

A first fluid, typically a buffer solution containing the analyte or a sample to be analyzed, is injected by injecting means through a first injection conduit, and a second fluid, typically a buffer solution, is injected by injecting means through a second injection conduit. The second fluid is typically used for rinsing the flow conduit system and filling it with liquid, and during the actual measurements for establishing a base sensor signal without binding (baseline), and for measuring the dissociation phase of the binding. Typically, the second fluid consists of a pH stabilized buffer, and can be based on buffers such as, but not limited to, phosphate buffered saline (PBS), 4-(2-hydroxyethyl)-1-piperazineethanesulfonic acid (HEPES) or 2-(N-morpholino) ethanesulfonic acid (MES). Typically, the first fluid containing the analyte or sample is based on the same buffer solution as the second fluid, such as the two fluids in principle only differ in analyte or sample concentration. The injection conduits are fluidly connected to the first inlet/outlet conduit by means of one or more, typically two, fluid junctions. The fluid junctions are characterized in that they are valveless, such as fluidic T-junctions or Y-junctions or four-way junctions, and by a maximum dead volume of less than 10 microliters. Preferably the maximum dead volume is less than 1 microliter. The dead volume is defined as the volume of the part of the first inlet/outlet conduit between the first end portion of the first flow cell conduit and the valveless junction which is positioned closest to the flow cell conduit.

Therefore according to the preferred embodiment of the preset invention there is provided a flow conduit system for contacting a first and a second fluid with one or more discrete sensing areas of a biochemical sensor, comprising; a first flow cell conduit comprising one or more sensing areas, a first inlet/outlet conduit operably connected to a first end portion of the first flow cell conduit, a second inlet/outlet conduit operably connected to a second end portion of the first flow cell conduit, a first selector valve interposed between the end portions of the first inlet/outlet conduit and having first and second positions for respectively at least close to completely allowing or not allowing passage of fluids between the end portions of the first inlet/outlet conduit, a second selector valve interposed between the end portions of the second inlet/outlet conduit and having first and second positions for respectively at least close to completely allowing or not allowing passage of fluids between the end portions of the second inlet/outlet conduit, a first injection conduit and a second injection conduit having first end portions operably connected to the first inlet/outlet conduit in between the first end portion of the first flow cell conduit and the first selector valve by means of one or more first valveless junctions, injecting means operably connected to second end portions of the first and second injection conduits for controllably injecting the first and second fluids into respectively the first and second injection conduits, a control unit for controlling the injection means and the first and second selector valves in a manner as to allow the first fluid to flow from the second end portion of the first injection conduit on a first and second flow path and to allow the second fluid to flow from the second end portion of the second injection conduit on a third and fourth flow path, wherein the first and third flow paths are defined by a flow to the second end portion of the first inlet/outlet conduit without contacting the sensing areas within the first flow cell conduit, and the second and fourth flow paths are defined by a flow through the first flow cell conduit to the second end portion of the second inlet/outlet conduit, wherein the volume between any of the valveless junctions and the first end portion of the first flow cell conduit is smaller than 10 microliters. Most preferably the volume between any of the valveless junctions and the first end portion of the first flow cell conduit is smaller than 1 microliter.

Thanks to the inventive arrangement with two injection conduits in fluid communication with valveless junctions, it is the dead volume between the first flow cell conduit and nearest valveless junction which dictates the fluid transition times in the first flow cell conduit and not the volume between the first flow cell conduit and active switching valves. Thus in the present invention the active switching valves can be positioned far from the first flow cell conduit and fast fluid transition times can still be achieved. By conducting the sample or analyte fluid close to the flow cell conduit in a separate channel and by proper sample preparation, such that the fluid containing the sample or analyte is at least close to undiluted at the corresponding valveless junction prior to sample fluid injection, mixing between the sample fluid and the neutral buffer fluid only occurs between the valveless junctions and the flow cell conduit. Within the typical time frames for biochemical sensor analysis of several minutes, and using typical channel geometries, no significant mixing effects such as through diffusion or turbulence occur close to or within the valveless junctions even without a physical barrier such as a membrane within a valve. Hence, only the volume between the valveless junction and the flow cell conduit corresponds now to the dead volume which needs to be "rinsed" during a sample transition, and thereby only this volume contributes to the transition time. Avoiding valves close to the flow cell conduits and thus close to the active sensor surfaces results in a huge cost benefit because expensive integrated microvalves such as described in WO0236485 are no longer needed. At the same time, using the inventive flow conduit system, a timing performance comparable to a system including integrated valves can be achieved through a small volume between the first flow cell conduit and a valveless junction even without integrated valves.

By placing the valveless junctions "close" to the flow cell conduit, a low dead volume i.e. a low volume between the flow cell conduit and the nearest valveless junction is provided. Thus a fast fluid transition can be achieved between the fluid in the first injection conduit and the fluid in the second injection conduit. Preferably the fluids within the injection conduits are and remain at least close to undiluted during the measurement so that upon injection into the flow cell conduit, the actual concentration of the analyte or sample corresponds well with the initial concentration.

Using a first selector valve and a second selector valve which can be placed further away from the sensing areas, the movement of fluids can be controlled by means of a control unit, which is adapted to selectively open and close the selector valves in a controlled manner and to control the injecting means in order to selectively inject fluid into the injection conduits. The control unit facilitates the preparation of the fluids in the injection conduits, and that the sensing areas can be successively contacted by the fluids, while the fluids within the injection conduits are and remain at least close to undiluted during the measurement.

In the present application the term "fluidly connected" means connected such that fluid communication can take place; for example if a component is said to be fluidly connected to another then it will be understood that fluid can be communicated between the components.

The flow conduit system may further comprise a second flow cell conduit comprising one or more sensing areas. In this embodiment, the second inlet/outlet conduit is operably connected to a first end portion of the second flow cell conduit, an intermediate conduit is operably connected to the second end portion of the first flow cell conduit and a second end portion of the second flow cell conduit, and an outlet conduit operably connected to the intermediate conduit by means of a second valveless junction. Also, a third selector valve is interposed between the end portions of the outlet conduit and having first and second positions for respectively at least close to completely allowing or not allowing passage of fluids between the end portions of the outlet conduit.

In this configuration with two flow cell conduits, a third injection conduit and a fourth injection conduit may further be introduced typically by mirroring the injection configuration, having first end portions operably connected to the second inlet/outlet conduit in between the first end portion of the second flow cell conduit and the second selector valve by one or more third valveless junctions, the fluids can be selectively either injected into the first flow cell conduit only, or the second flow cell conduit only, or into the first and then the second flow cell conduit in series or vice-versa, or the flow cell conduits can be completely bypassed.

Therefore, the injecting means is operably connected to second end portions of the third and fourth injection conduits for controllably injecting the first and second fluids into respectively the first or third and second or fourth injection conduits, wherein the control unit is adapted to control the injection means and the first and second and third selector valves in a manner as to allow the first fluid to flow from the second end portion of the first injection conduit on the first and the second and a fifth flow path and from the second end portion of the third injection conduit on a sixth and a seventh and an eight flow path and to allow the second fluid to flow from the second end portion of the second injection conduit on the third and the fourth and a ninth flow path and from the second end portion of the fourth injection conduit on a tenth and an eleventh and a twelfth flow path. There, the fifth and the ninth flow paths are defined by a flow through the first flow cell conduit to the second end portion of the outlet conduit without contacting the sensing areas within the second flow cell conduit, and the sixth and the tenth flow paths are defined by a flow to the second end portion of the second inlet/outlet conduit without contacting the sensing areas within the second or first flow cell conduits, and the seventh and the eleventh flow paths are defined by a flow through the second and first flow cell conduits to the second end portion of the first inlet/outlet conduit, and the eight and twelfth flow paths are defined by a flow through the second flow cell conduit to the second end portion of the outlet conduit without contacting the sensing areas within the first flow cell conduit.

Therefore in a further embodiment the flow conduit system may further comprise a second flow cell conduit which comprises one or more sensing areas for biochemical sensing, which is fluidly connected to the first flow cell conduit.

The flow conduit system may further comprise an intermediate conduit which fluidly connects the second flow cell conduit to the first flow cell conduit.

The flow conduit system may further comprise third selector valve fluidly connected to the intermediate conduit by means of an outlet conduit.

Preferably the outlet conduit is fluidly connected to the intermediate conduit by means of a valveless junction.

Preferably the control unit is further configured to control the third selector valve.

Preferably the third selector valve is further fluidly connected to a receptacle which can hold fluids.

Preferably the flow conduit system further comprises a second inlet/outlet conduit fluidly connected to the second flow cell conduit; and a second selector valve, wherein the second inlet/outlet conduit fluidly connects the second flow cell conduit to the second selector valve.

Preferably the flow conduit system further comprises, a third injection conduit having a first end and a second end; a fourth injection conduit having a first end and a second end; and wherein the fluid injecting means is further fluidly connected to the second ends of each of the third and fourth injection conduits so that the fluid injecting means can selectively inject fluids into the third and/or fourth injection conduits, and wherein the third injection conduit is fluidly connected, at its first end, to the second inlet/outlet conduit by a valveless junction, and the fourth injection conduit is fluidly connected, at its first end, to the second inlet/outlet conduit by a valveless junction.

The third injection conduit may be fluidly connected, at its first end, to the second inlet/outlet conduit by a third valveless junction, and the fourth injection conduit may be fluidly connected, at its first end, to the second inlet/outlet conduit by a fourth valveless junction. In this case each of the first and second valveless junctions is are preferably three-way junctions.

The third injection conduit may be fluidly connected, at its first end, to the second inlet/outlet conduit by a valveless junction, and the fourth injection conduit may be fluidly connected, at its first end, to the second inlet/outlet conduit by the same valveless junction. In this case a single valveless junction is provided which is preferably a four-way junction.

It will be understood that at three-way junction is a junction which provides three flow paths and a four-way junction is a junction which provides four flow paths.

Preferably the third and fourth injection conduits are each valveless. Preferably the portion of the second inlet/outlet conduit which is between the second flow cell conduit and the or each valveless junction is valveless. Preferably the portion of the third inlet/outlet conduit which is between the second flow cell conduit and the third valveless junction is valveless. Preferably the portion of the first inlet/outlet conduit which is between the second flow cell conduit and the fourth valveless junction is valveless.

Therefore in the most preferred embodiment the flow conduit system further comprises a second flow cell conduit comprising one or more sensing areas wherein the second inlet/outlet conduit is operably connected to a first end portion of the second flow cell conduit, an intermediate conduit operably connected to the second end portion of the first flow cell conduit and a second end portion of the second flow cell conduit, an outlet conduit operably connected to the intermediate conduit by means of a second valveless junction, a third selector valve interposed between the end portions of the outlet conduit and having first and second positions for respectively at least close to completely allowing or not allowing passage of fluids between the end portions of the outlet conduit, wherein the control unit is adapted to control the injection means and the first and second and third selector valves in a manner as to allow the first fluid to flow from the second end portion of the first injection conduit on the first and the second and a fifth flow path and to allow the second fluid to flow from the second end portion of the second injection conduit on the third and the fourth and a ninth flow path wherein the fifth and the ninth flow paths are defined by a flow through the first flow cell conduit to the second end portion of the outlet conduit without contacting the sensing areas within the second flow cell conduit.

Most preferably this further embodiment forms a symmetrical flow conduit system comprising a third injection conduit and a fourth injection conduit having first end portions operably connected to the second inlet/outlet conduit in between the first end portion of the second flow cell conduit and the second selector valve by one or more third valveless junctions, wherein the injecting means is operably connected to second end portions of the third and fourth injection conduits for controllably injecting the first and second fluids into respectively the first or third and second or fourth injection conduits, wherein the control unit is adapted to control the injection means and the first and second and third selector valves in a manner as to allow the first fluid to flow from the second end portion of the first injection conduit on the first and the second and the fifth flow path and from the second end portion of the third injection conduit on a sixth and a seventh and an eight flow path and to allow the second fluid to flow from the second end portion of the second injection conduit on the third and the fourth and the ninth flow path and from the second end portion of the fourth injection conduit on a tenth and an eleventh and a twelfth flow path, wherein the sixth and the tenth flow paths are defined by a flow to the second end portion of the second inlet/outlet conduit without contacting the sensing areas within the second or first flow cell conduits, and the seventh and the eleventh flow paths are defined by a flow through the second and first flow cell conduits to the second end portion of the first inlet/outlet conduit, and the eight and twelfth flow paths are defined by a flow through the second flow cell conduit to the second end portion of the outlet conduit without contacting the sensing areas within the first flow cell conduit.

In each of the above mentioned embodiments it will be understood that each of the first, second, third and fourth valveless junctions may be defined by three-way conduit. For example, each of the first, second, third and fourth valveless junction may be T-shaped conduit or Y-shaped conduit.

Each of the first, second, third and fourth valveless junctions may be defined by a three-way conduit connector.

Each of the first, second, third and fourth valveless junctions may be a T-shaped conduit connector or Y-shaped conduit connector. A conduit connector is any member which can fluidly connect two or more conduits and is valveless.

The first and second valveless junctions and the first fluid flow cell conduit may each comprise connecting means which enable them to be removably attached within the flow conduit system.

The third and fourth valveless junctions and the second fluid flow cell conduit may each comprise connecting means which enable them to be removably attached within the flow conduit system.

Alternatively each of the first and second valveless junctions may be defined by a single four-way conduit and the third and fourth valveless junctions may be defined by another single four-way conduit. For example, the first and second valveless junction may be a H-shaped conduit and the third and fourth valveless junction may be another H-shaped conduit. Each of the four-way conduits may comprise connecting means which enable them to be removably attached within the flow conduit system.

In a further preferred embodiment, the flow conduit system is divided into a removable part of the flow conduit system and a fixed part of the flow conduit system. The removable part of the flow conduit system is preferably integrated into a cartridge for a biochemical sensor wherein the cartridge can be removeably attached to a fixed biochemical sensor component comprising the fixed part of the flow conduit system, so that the cartridge is in operable connection with the fixed biochemical sensor component. Typically, the removable flow conduit system comprises the flow cell conduits comprising one or more sensing areas. By combining the sensing areas and the flow cell conduits into one element which may be disposable, the sensing areas are protected since it is not directly exposed prior to cartridge insertion. Also, the issue of clogging is less frequent and does not result in high maintenance costs, since the flow cell conduits are exchanged every time the sensor transducer is exchanged.

Thus in each of the flow conduit systems mentioned above a valveless junction and the first flow cell conduit may be provided on a single cartridge. The valveless junction and the first flow cell conduit integral to the single cartridge.

The single cartridge may comprise a fixed portion and a flexible cantilever which is attached to the fixed portion at one end and which has a free end which can be flexed to move relative to the fixed portion, wherein the valveless junction and first flow cell conduit are provided on the flexible cantilever.

The single cartridge may comprise connecting means which are configured to allow the single cartridge to be removeably attached to the flow conduit system, so that the valveless junction and first flow cell conduit can be selectively removed from the flow conduit system.

Preferably at least the first valveless junction, the second valveless junction and the first flow cell conduit may be all provided on a single cartridge. The first valveless junction, the second valveless junction and the first flow cell conduit may be all integral to a single cartridge.

The single cartridge may comprise a fixed portion and a flexible cantilever which is attached to the fixed portion at one end and which has a free end which can be flexed to move relative to the fixed portion, wherein the first valveless junction, the second valveless junction and first flow cell conduit are provided on the flexible cantilever.

The single cartridge may comprise connecting means which are configured to allow the single cartridge to be removeably attached to the flow conduit system, so that the first and second valveless junctions and first flow cell conduit can be selectively removed from the flow conduit system.

The third valveless junction, the fourth valveless junction and the second flow cell conduit may be further all provided on the single cartridge.

The third valveless junction, the fourth valveless junction and the second flow cell conduit may be all integral to the single cartridge.

The second flow cell conduit may be provided on the flexible cantilever of the single cartridge.

The single cartridge may comprise connecting means which are configured to allow the single cartridge be removeably attached to the flow conduit system, so that the first and second valveless junctions, first flow cell conduit, and the third valveless junction, the fourth valveless junction and the second flow cell conduit, can be removeably attached within the flow conduit system.

The flow conduit system may further comprise a readout means for recording a sensor signal from one or more sensing areas provided in the first flow cell conduit.

The flow conduit system may further comprise a readout means for recording a sensor signal from one or more sensing areas provided in the second flow cell conduit.

There is further provided a cartridge comprising a valveless junction and a first flow cell conduit.

Preferably the cartridge comprises a first valveless junction, a second valveless junction and a first flow cell conduit.

The cartridge may further comprise a third valveless junction, a fourth valveless junction and a second flow cell conduit.

The cartridge may further comprise connecting means which are configured to allow the cartridge to be removeably attached to a flow conduit system.

The cartridge may further comprise a fixed portion and a flexible cantilever which is attached to the fixed portion at one end and which has a free end which can be flexed to move relative to the fixed portion, wherein the first flow cell conduit is provided on the flexible cantilever.

The valveless junction may be further provided on the flexible cantilever. Preferably the first valveless junction and second valveless junction may be further provided on the flexible cantilever.

The second flow cell conduit may be further provided on the flexible cantilever.

The third valveless junction and a fourth valveless junction may be further provided on the flexible cantilever.

Preferably the cartridge is a cartridge for a biochemical sensor comprising a removable part of the flow conduit system, wherein the cartridge can be removably attached to a fixed biochemical sensor component comprising a fixed part of the flow conduit system, so that the cartridge is in operable connection with the fixed biochemical sensor component, wherein the removable flow conduit system and the fixed flow conduit system together comprise a flow conduit system according to any one of the above-mentioned conduit systems, and wherein the removable flow conduit system comprises the first flow cell conduit comprising one or more sensing areas In a preferred embodiment of the cartridge according to the invention, the removable part of the flow conduit system is configured to be movable in a direction at least close to perpendicular to the surface of the sensing areas by means of at least one positioning cantilever integrally formed into the cartridge.

According to the invention, there is further provided a biochemical sensor device comprising a flow conduit system according to any one of the above-mentioned flow conduit systems.

The biochemical sensor device may further comprise a cartridge according to any of the above-mentioned cartridges.

Preferably the biochemical sensor device comprises the inventive flow conduit system, which preferably comprises readout means such as based on SPR, waveguides or Surface-Acoustic Waves, for recording a sensor signal from the one or more sensing areas, and optionally comprises a cartridge with a removable part of the flow conduit system.

According to a further aspect of the present invention there is provided a first method for performing biochemical sensing, using a flow conduit system according to the present invention, the method comprising the steps of, (a) filling the flow conduit system with buffer fluid; (b) opening the first selector valve; (c) using the injecting means to inject a sample fluid which contains molecules to be sensed, into the second injection conduit; (d) using said buffer fluid to restrict the flow of the sample fluid from the second injection conduit into the first inlet/outlet conduit; (e) using the injection means to inject buffer fluid into the first injection conduit and flowing the buffer fluid along the first injection conduit, into the first inlet/outlet conduit, and through the first selector valve; (f) stopping the injection means from injecting the buffer fluid; (g) closing the first selector valve; (h) using the injection mean to inject more sample fluid which contains molecules to be sensed, into the second injection conduit, so that the sample fluid flows through the first flow cell conduit; (i) using the first flow cell conduit to sense the amount of said molecules to be sensed which have bound to sensing areas or to molecules bound to the sensing areas of the first flow cell conduit, typically by reading out and recording a corresponding sensor signal and successively analyzing the resulting measurement curves.

The method may further comprise the steps of, flowing a further buffer fluid, which can cause the sensed molecules to disassociate from sensing areas in the first flow cell conduit, through the flow cell conduit; and measuring the disassociation of the sensed molecules.

The method may further comprise the step of outputting a signal from the first flow cell conduit which is indicative of the amount of said molecules to be sensed which have bound to sensing areas of the first flow cell conduit.

In another method for performing biochemical sensing, according to the present invention comprises the steps of, (a) performing the steps (a)-(h) of the first method for performing biochemical sensing mentioned above; (b) sensing background fluctuations in the sample as the sample is flowing through the first flow cell conduit; (c) outputting a signal from the first flow cell conduit which is indicative of the background fluctuations in the sample; (d) flowing the sample through the second flow cell conduit; (f) sensing the amount of said molecules to be sensed which have bound to sensing areas of the second flow cell conduit as the sample is flowing through the second flow cell conduit; (g) outputting a signal from the second flow cell conduit which is indicative of the amount of molecules to be sensed which have bound to sensing areas of the second flow cell conduit; (f) subtracting the signal output by the first flow cell conduit from the signal output be the second flow cell conduit.

It will be understood that any either of the first or second flow cell conduits may be used for sensing background fluctuations, while the other flow cell conduit being used for sensing the amount of said molecules to be sensed. Accordingly the method may comprise the steps of (a) performing the steps (a)-(h) of the method of first method for performing biochemical sensing, using the second flow cell conduit when performing step (h); (b) sensing background fluctuations in the sample as the sample is flowing through the second flow cell conduit (c) outputting a signal from the second flow cell conduit which is indicative of the background fluctuations in the sample; (d) flowing the sample through the first flow cell conduit; (f) sensing the amount of said molecules to be sensed which have bound to sensing areas of the second flow cell conduit as the sample is flowing through the first flow cell conduit; (g) outputting a signal from the first flow cell conduit which is indicative of the amount of molecules to be sensed which have bound to sensing areas of the second flow cell conduit; (f) subtracting the signal output by the second flow cell conduit from the signal output be the first flow cell conduit.

There is further provided another method for performing biochemical sensing, the method comprising the steps of, (a) filling the flow conduit system with buffer fluid; (b) opening the first selector valve; (c) using the injecting means to inject a sample fluid which contains molecules to be sensed, into the injection conduit whose first end is connected to the first inlet/outlet conduit by a first valveless junction which is located closest to the first flow cell conduit; (d) using said buffer fluid to restrict the flow of the sample fluid from the said injection conduit into the first inlet/outlet conduit; (e) using the injection means to inject buffer fluid into either the third or fourth injection conduit and flowing the buffer fluid along the second inlet/outlet conduit, through the second flow cell conduit, through the first flow cell conduit and through the selector valve; (f) stopping the injection means from injecting the buffer fluid; (g) closing the first selector valve; (h) using the injection means to inject more sample fluid which contains molecules to be sensed, into said injection conduit used in step (c) so that the sample fluid flows into the first flow cell conduit via the valveless junction which is located closest to the first flow cell conduit; (i) using the first flow cell conduit to sense the amount of said molecules to be sensed which have bound to sensing areas of the first flow cell conduit, typically by reading out and recording a corresponding sensor signal and successively analyzing the resulting measurement curves.

The method may further comprise the step of outputting a signal from the first flow cell conduit which is indicative of the amount of said molecules to be sensed which have bound to sensing areas of the first flow cell conduit The method may further comprise the steps of, flowing a further buffer fluid, which can cause the sensed molecules to disassociate from sensing areas in the first flow cell conduit, through the flow cell conduit; and measuring the disassociation of the sensed molecules.

Advantageously each of the above-mentioned method involve the steps of using a buffer fluid to restrict the flow of the sample fluid, accordingly this obviates the needs for valves to be positioned close to any of the flow cell conduits.

In an embodiment of a method for operating a biochemical sensor according to the invention, both injection conduits are first prepared by filling with two separate fluids without contacting any of the flow cell conduits, then one or both of the flow cell conduits are sequentially contacted with both fluids while recording a sensor signal. The operating routine consists in the following steps. First, a controlled volume of the first fluid is injected into the first flow path without contacting the sensing areas within the first or second flow cell conduit, in a manner as to raise the concentration of the first fluid in the first injection conduit at the valveless junction to the first inlet/outlet conduit to at least close to 100%. Typically, the first fluid contains the sample or analyte molecules, and in this context a concentration of 100% of the first fluid refers to the initial concentration of the sample or analyte within the first fluid prior to the injection into the first injection conduit, meaning that the sample or analyte is not diluted by fluids already present in the flow conduits or fluids injected through the second injection conduit. This is typically achieved by opening the first selector valve and closing the second selector valve, such as there is no motion of the typically incompressible fluid within the flow cell conduit, and that all of the fluid injected into the first injection conduit by the injecting means flows through the first selector valve and not through the flow cell conduit. Optionally, the first fluid can be separated using airgaps from any fluid before and after the first fluid. In this context, airgaps are small plugs of air separating two volumes of fluid, allowing fluid separation without mixing, and which are typically formed by aspiration of air between two fluid segments within the injection means.

Then, in order to clean the conduits from excess parts of the first fluid, which typically consists in the remaining parts of the first fluid present in the first inlet/outlet conduit which will not be used in the analysis and which would typically disturb the baseline through a presence of analyte or sample, and in order to raise the concentration of the second fluid within the first inlet/outlet conduit to at least close to 100%, a controlled volume of the second fluid is injected into the third flowpath without contacting the sensing areas within the first or second flow cell conduit.

During these first two steps, the first switching valve is typically open and the second switching valve is typically closed.

Then, while recording the sensor signal, first the second fluid and then the first fluid and then again the second fluid are injected through the first or first and second flow cell conduit in a manner as to contact the one or more sensing areas with the respective fluids sequentially. During these steps, if injected through all flow cell conduits in series, the first switching valve is typically closed and the second switching valve is typically open and the optional third switching valve is closed. Alternatively, if injected through the first flow cell conduit only, the first and second switching valves are typically closed and the third switching valve is open.

An embodiment of the method may comprise the steps of:
Injecting a controlled volume of the first fluid having optionally separating airgaps into the first flow path without contacting the sensing areas within the first or second flow cell conduit, in a manner as to raise the concentration of the first fluid in the first injection conduit at the valveless junction to the first inlet/outlet conduit to at least close to 100%
Injecting a controlled volume of the second fluid into the third flowpath without contacting the sensing areas within the first or second flow cell conduit, in a manner as to raise the concentration of the second fluid within the first inlet/outlet conduit to at least close to 100%
Injecting the second fluid into the ninth or fourth flowpath through the first or first and second flow cell conduit in a manner as to contact the one or more sensing areas with the second fluid during a first controlled amount of time
Recording the sensor signal during the first controlled amount of time
Injecting the first fluid into the fifth or second flowpath through the first or first and second flow cell conduit in a manner as to contact the one or more sensing areas with the first fluid during a second controlled amount of time
Recording the sensor signal during the second controlled amount of time
Injecting the second fluid into the ninth or fourth flowpath through the first or first and second flow cell conduit in a manner as to contact the one or more sensing areas with the second fluid during a third controlled amount of time
Recording the sensor signal during the third controlled amount of time.

In an embodiment of a method according to the present invention in which the separation of fluid flow is further improved by applying a counter-flow during the preparation steps and optionally during the measurement. The method comprises the following steps. First, a controlled volume of the first fluid having optionally separating airgaps is injected into the first flow path without contacting the sensing areas within the first or second flow cell conduit, in a manner as to raise the concentration of the first fluid in the first injection conduit at the valveless junction to the first inlet/outlet conduit to at least close to 100%. Simultaneously, in order to raise the concentration of the second fluid within the first inlet/outlet conduit to at least close to 100%, and in order to exclude any spill of the first fluid into the flow cell conduits, a controlled volume of the second fluid is injected into the eleventh flowpath through the first and second flow cell conduits, thus creating a counter-flow. Preferably, the counter flow with the second fluid is applied for a slightly longer period of time than the injection of the first fluid in order to well rinse the conduits. During these steps, the first switching valve is typically open and the second switching and third valves are typically closed.

Then, while recording the sensor signal, first the second fluid and then the first fluid and then again the second fluid are injected through the first or first and second flow cell conduit in a manner as to contact the one or more sensing areas with the respective fluids sequentially. During these steps, if injected through the first and second flow cell conduits in series, the first switching valve is typically closed and the second switching valve is typically open and the third switching valve is closed. Alternatively, if injected through the first flow cell conduit only, the first and second switching valves are typically closed and the third switching valve is open.

The method may comprise the steps of:

Injecting a controlled volume of the first fluid having optionally separating airgaps into the first flow path without contacting the sensing areas within the first or second flow cell conduit, in a manner as to raise the concentration of the first fluid in the first injection conduit at the valveless junction to the first inlet/outlet conduit to at least close to 100%

Simultaneously injecting a controlled volume of the second fluid into the eleventh flowpath through the first and second flow cell conduits Injecting the second fluid into the ninth flowpath or the fourth flowpath through respectively the first or first and second flow cell conduits, in a manner as to contact the one or more sensing areas with the second fluid during a first controlled amount of time Recording the sensor signal during the first controlled amount of time Injecting the first fluid into the fifth or the second flowpath through respectively the first or first and second flow cell conduits, in a manner as to contact the one or more sensing areas with the first fluid during a second controlled amount of time Recording the sensor signal during the second controlled amount of time Injecting the second fluid into the ninth flowpath or the fourth flowpath through respectively the first or first and second flow cell conduits, in a manner as to contact the one or more sensing areas with the second fluid during a third controlled amount of time Recording the sensor signal during the third controlled amount of time.

In a further embodiment of a method according to the invention, a counter-flow is also applied when contacting only the sensing areas within one of the two flow cell conduits with the first fluid. The method therefore comprises the following step. While simultaneously injecting a controlled volume of the first fluid into the fifth flowpath through the first flow cell conduit, a controlled volume of the second fluid is injected into the eighth flowpath through the second flow cell conduit, in a manner as to simultaneously contact the one or more sensing areas within the first flow conduit with the first fluid and to contact the one or more sensing areas within the second flow conduit with the second fluid. Thus the method may comprise the steps of simultaneously injecting a controlled volume of the first fluid into the fifth flowpath through the first flow cell conduit and injecting a controlled volume of the second fluid into the eighth flowpath through the second flow cell conduit, in a manner as to simultaneously contact the one or more sensing areas within the first flow conduit with the first fluid and to contact the one or more sensing areas within the second flow conduit with the second fluid.

The methods can be applied in a mirror-like fashion, for a biosensor having a symmetrical flow conduit system, for contacting the sensing areas within the second flowcell first, by replacing the first and second injection conduits by their counterparts third and fourth injection conduits, and replacing the first inlet/outlet conduit with the second inlet/outlet conduit, and replacing the first switching valve with the second switching valve and vice-versa as well as replacing the flow path numbers by their symmetrical counterpart.

BRIEF DESCRIPTION OF THE DRAWINGS

In the following, the object of the invention is explained in more detail on the basis of preferred examples of embodiments, which are illustrated in the annexed drawings. They respectively schematically depict.

DETAILED DESCRIPTION OF THE INVENTION

Figure 1:
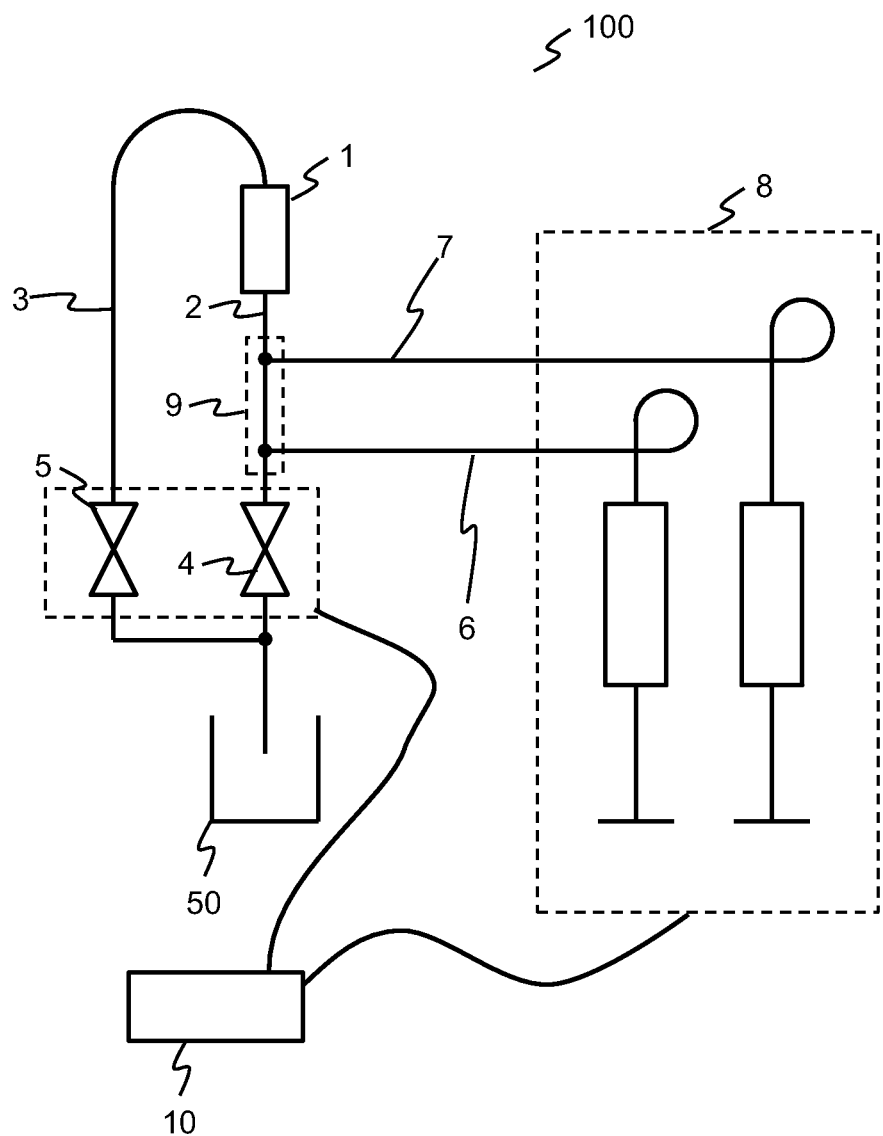
FIG. 1 Schematic view of a flow conduit system having one flow cell

FIG. 1 illustrates a schematic view of a flow conduit system (100) for a biochemical sensor having one flow cell conduit (1). The flow cell conduit (1) comprises one or more sensing areas. Preferably, the sensing areas are functionalized such as to selectively bind a ligand, or are prepared to allow selective functionalization. Such a surface preparation may comprise a dextran matrix with carboxymethylated groups, such as known to the skilled in the art. The sensing areas can be but are not limited to part of a flat surface or chip, such as is the case for SPR or waveguide-based or SAW sensors, or can be at a tip of an optical fiber, or the outer surface of a nanowire. The sensor transducer and readout scheme preferably corresponds to the sensor described in WO 2008110026. The transducer may also be based on but is not limited to SPR, other (interferometric) waveguide, surface acoustic waves (SAW), Quartz Crystal Microbalance (QCM), or fully electronic schemes such as nanowire-based transducers.

A first inlet/outlet conduit (2) is operably connected to a first end portion of the first flow cell conduit (1), and a second inlet/outlet conduit (3) is operably connected to a second end portion of the first flow cell conduit (1). The conduits can be, but are not limited to, microfluidic channels or tubes.

A first selector valve (4) is interposed between the end portions of the first inlet/outlet conduit (2), allowing (open) or not allowing (closed) passage of fluids between the end portions of the first inlet/outlet conduit (2). A second selector valve (5) is interposed between the end portions of the second inlet/outlet conduit (3), allowing (open) or not allowing (closed) passage of fluids between the end portions of the second inlet/outlet conduit (3). The selector valves can be, but are not limited to, solenoid valves or rotary valves or membrane valves. Preferably, the selector valves have a low switching volume below 100 microliters. Most preferably, the selector valves have a low switching volume below 10 microliters.

A first injection conduit (6) and a second injection conduit (7) are operably connected to the first inlet/outlet conduit (2) in between the first end portion of the first flow cell conduit (1) and the first selector valve (4) by means of one or more first valveless junctions (9). The valveless junctions can be of any type known to the skilled in the art, such as T-junctions or Y-junctions.

Furthermore, injecting means (8) are operably connected to second end portions of the first and second injection conduits (6, 7) for controllably injecting the first and second fluids into respectively the first and second injection conduits (6, 7). The injecting means (8) typically comprise a fluidic system of pumps, valves and sample loops, and may comprise automated sample pickup systems such as autosamplers or xyz sample pickup stages. The injecting means (8) may also comprise ports for manual sample injection such as a syringe port.

A control unit (10) controls the injection means (8) either automatically or in case of manual injection by indicating the time for injection, preferably through a visual or auditive signal. The control unit (10) furthermore controls the first and second selector valves (4,5). It may comprise but is not limited to analog or digital electronics comprising one or several microcontrollers, personal computers or application-specific integrated circuits (ASIC). Typically, the selector valves (4,5) and injection means (8) are controlled by the control unit (10) through a serial interface, or by appropriate voltages or voltage pulses. By opening the first selector valve (4) and closing the second selector valve (5), the flow cell conduit (1) is bypassed. The first fluid is thereby flown on a first flow path when injecting into the first injection conduit (6) when the first selector vale (4) is opened and the second selector valve (5) is closed, and the second fluid is flown on a third flow path when injecting into the second injection conduit (7) when the first selector valve (4) is opened and the second selector valve (5) is closed. The first flow path is defined by a flow from the first injection conduit (6) to the second end portion of the first inlet/outlet conduit (2), and the third flow path is defined by a flow from the second injection conduit (7) to the second end portion of the first inlet/outlet conduit (2). Typically, the neutral buffer solution is injected through the second injection conduit (7) and the fluid containing the analyte or sample is injected through the first injection conduit (6). These flow paths are typically used for fluid preparation using the corresponding fluid preparation steps detailed below, with the goal that the fluid containing the analyte is present in the corresponding injection conduit and valveless junction at least close to undiluted, and without contacting the sensing areas within the first flow cell conduit (1) during that preparation step. To achieve this, typically, first a controlled volume, typically three to five times the volume of the first injection conduit (6), of the first fluid containing the sample or analyte is flown on the first flow path, such as the first injection conduit (6) is rinsed with the first fluid and that at the end of the injection the first fluid is close to undiluted within the second injection conduit (6) including the corresponding valveless junction (9), followed by flowing a small volume, such as 0.1 to 10 microliters, of the second fluid being a neutral buffer solution on the third flow path in order to rinse the first inlet/outlet conduit (2) from the first fluid. As a result of this preparation step, the first injection conduit (6) is filled with the first fluid up to the corresponding valveless junction, and the first inlet/outlet conduit (2) is filled with the second fluid, effectively creating a fluid interface between the two fluids at the corresponding valveless junction. Preferably, for a good definition of the fluid interface, the valveless junction of the second injection conduit (7) used for injection of the neutral buffer solution is placed closer to the first flow cell conduit (1) than the valveless junction of the first injection conduit (6) used for injection of the analyte or sample. Preferably, the last rinsing step is carried out at a flow rate below 1 milliliter per second, most preferably below 100 microliters per second, in order not to excessively rinse the first fluid at the corresponding valveless junction (9), i.e. not pushing the interface between the first and second fluids further into the first injection conduit (6), which would increase the volume to be traveled for the first liquid upon later injection into the flow cell conduit (1), which would result in longer fluid transition times. Surprisingly, this fluid interface is relatively stable even when subject to pressure differences occurring during the switching operations of the selector valves (4,5). This is achieved through the previous filling of the flow conduit system with neutral buffer fluid, such as the back pressure of the incompressible buffer fluid restricts the movement of the fluid interface.

By closing the first selector valve (4) and opening the second selector valve (5), the fluids can be injected into the flow cell conduit (1) for an actual measurement such as a kinetic measurement, typically after the fluid preparation step has been executed, and using the measurement steps described below. The first fluid is thereby flown on a second flow path when injecting into the first injection conduit (6), and the second fluid is flown on a fourth flow path when injecting into the second injection conduit (7). The second flow path is defined by a flow from the first injection conduit (6) through the first flow cell conduit (1) to the second end portion of the second inlet/outlet conduit (3), and the fourth flow path is defined by a flow from the second injection conduit (7) through the first flow cell conduit (1) to the second end portion of the second inlet/outlet conduit (3). Typically, the second end portion of the second inlet/outlet conduit (3) is fluidly connected to a waste receptacle (50) to receive the fluids.

In a kinetic measurement and after the fluid preparation step has been executed, typically first the sensor surface within the first flow cell conduit (1) is contacted with the second fluid being a neutral buffer solution on the fourth flow path in order to establish and measure the baseline by reading out and recording the corresponding sensor signal, followed by contacting the sensor surface within the first flow cell conduit (1) with the first fluid containing the actual analyte or sample (such as an antigen) on the second flow path such as binding of the analyte to sensor bound ligands can occur during the association phase and can be measured by reading out and recording the corresponding sensor signal. Typically, afterwards the dissociation phase of the analyte from the to sensor bound ligands is measured by switching back to contacting the sensor surface with the second fluid so that a dissociation of the analyte or sample from the surface bound ligand can be measured by reading out and recording the corresponding sensor signal. Typically, the sensor signal is proportional to the amount of analyte or sample molecules, and the kinetic rates of the molecular binding is calculated by fitting the time-dependent amount of surface bound molecules to a kinetic model, such as the 1:1 Langmuir interaction model. Alternatively, the amount of surface bound molecules is or a time-dependent characteristic of the sensor signal, such as the initial slope during the association phase, is used to determine the sample or analyte concentration. This can be achieved with or without a prior calibration as is known to the skilled in the art. In the inventive fluid arrangement, the switching between contacting the flow cell conduit (1) with the first fluid and the second fluid, and vice versa is typically obtained by stopping the pump associated with the first injection conduit thereby stopping the flow of the first fluid, followed by starting the pump associated with the second injection conduit thereby starting the flow of the second fluid, and vice versa. An advantage of this procedure over existing methods is that no valve action is involved in the switching between the first and the second fluids, so that no artifacts originating from mechanical vibrations or acute pressure changes occur within the sensor signals.

Typically, after a measurement, all flow conduits are rinsed using the second fluid containing neutral buffer solution by corresponding rinsing steps. They typically consist in first emptying the first fluid on the first flow path, followed by flowing a relatively large amount, such as 100 microliters or more, of the second fluid on the third flow path.

Typically, for a complete analysis, the fluid preparation steps, the measurement steps and the rinsing steps are executed several times one after the other, first optionally using activation fluid as first fluid, such as a 50:50 mix of ethyl(dimethylaminopropyl) carbodiimide (EDC) and N-Hydroxysuccinimide (NHS) for an activation of the sensor surface which is typically functionalized using carboxymethyl groups to which a ligand can be bound after the optional activation, then using the ligand such as a drug target in a suitable concentration as first fluid for binding the ligand to the sensor surface, then using a passivation fluid such as Ethanolamine as first fluid for a passivation of remaining activated sites at the sensor surface without ligand bound, and then using successively different concentrations of the analyte or sample to be measured as first fluid in order to measure the actual binding between ligand and analyte. Optionally, regeneration fluids such as NaOH can be used as first fluid for regenerating the sensor surface, i.e. washing away unwanted bound molecules, after binding the ligand to the sensor surface or after binding the analyte or sample to the ligand.

Surprisingly, the dilutive or mixing effects on the first fluid in the first injection conduit (6) occurring within the first inlet/outlet conduit (2) between the valveless junctions and the first flow cell conduit (1) when flowing the second and typically different fluid through the valveless junction of the first injection conduit (6) with the first inlet/outlet conduit (2), and vice-versa, can be held small enough for the application of biosensors. By keeping the volume of the first inlet/outlet conduit (2) between the valveless junctions and the first flow cell conduit (1) small, such as 0.1 microliter or 1 microliter or 10 microliters, the fluid transition times at the first flow cell conduit (1) when switching between the fluids, can be typically be reduced to the order of fractions of seconds or seconds. This can typically be achieved by a small cross-section of the injection conduits (6,7), such as a few square microns to one square millimeter. Preferably the cross-section of each of the injection conduits (6,7), is between 100 square microns and 1 mm². Most preferably the cross-section of each of the injection conduits (6,7), is between 1000 square microns and 0.1 mm². Assuming a perfect preparation of the fluids at the valveless junctions (100% of the first fluid in the first injection conduit (6) without dilutive effects, and 100% of the second fluid in the second injection conduit (7) without dilutive effects), the transition times between the second and first fluid, typically depends on flowrates and dead volume between the valveless junctions (9) and the flow cell conduit (1). In this context, the transition time is apparent when switching from injecting the second fluid from the second injection conduit (7) into the flow cell conduit (1) on the fourth flow path to injecting the first fluid from first injection conduit (6) into the flow cell conduit (1) on the second flow path, and vice-versa i.e. when the second switching valve (5) is open and the first switching valve (4) is closed. These transitions typically occur in a kinetic measurement when switching from the baseline to the association phase, and when switching from the association phase to the dissociation phase. Typical flowrates during label-free assays are around 10 microliters/min to 100 microliters/min. The following Table 1 summarizes the dependency of transition time on dead volume between the valveless junctions (9) and the flow cell conduit (1) at a flowrate of 30 microliters/min, assuming that the first inlet/outlet conduit (2) is to be rinsed by a volume of three times its dead volume by the new fluid for the transition to be completed.

Knowing that the time scales of the binding events to be monitored, such as ligand-analyte association or dissociation, are within the range of seconds to minutes, it follows that if the volume between any of valveless junctions (9) and the first flow cell conduit (1) is reduced to 10 microliters or 1 microliters, the transition times are reduced to approximately 6 seconds or 0.6 seconds.

TABLE 1

Approximate fluid transition times vs. dead volume at a flowrate of 30 microliters/min

| Dead volume (microliters) | Transition time (s) |
| --- | --- |
| 0.1 | 0.6 |
| 1 | 6 |
| 10 | 60 |
| 100 | 600 |

In order to reduce this dead volume, the cross-section of the conduit can be kept small, and or the conduit length can be limited.

Figure 2A:
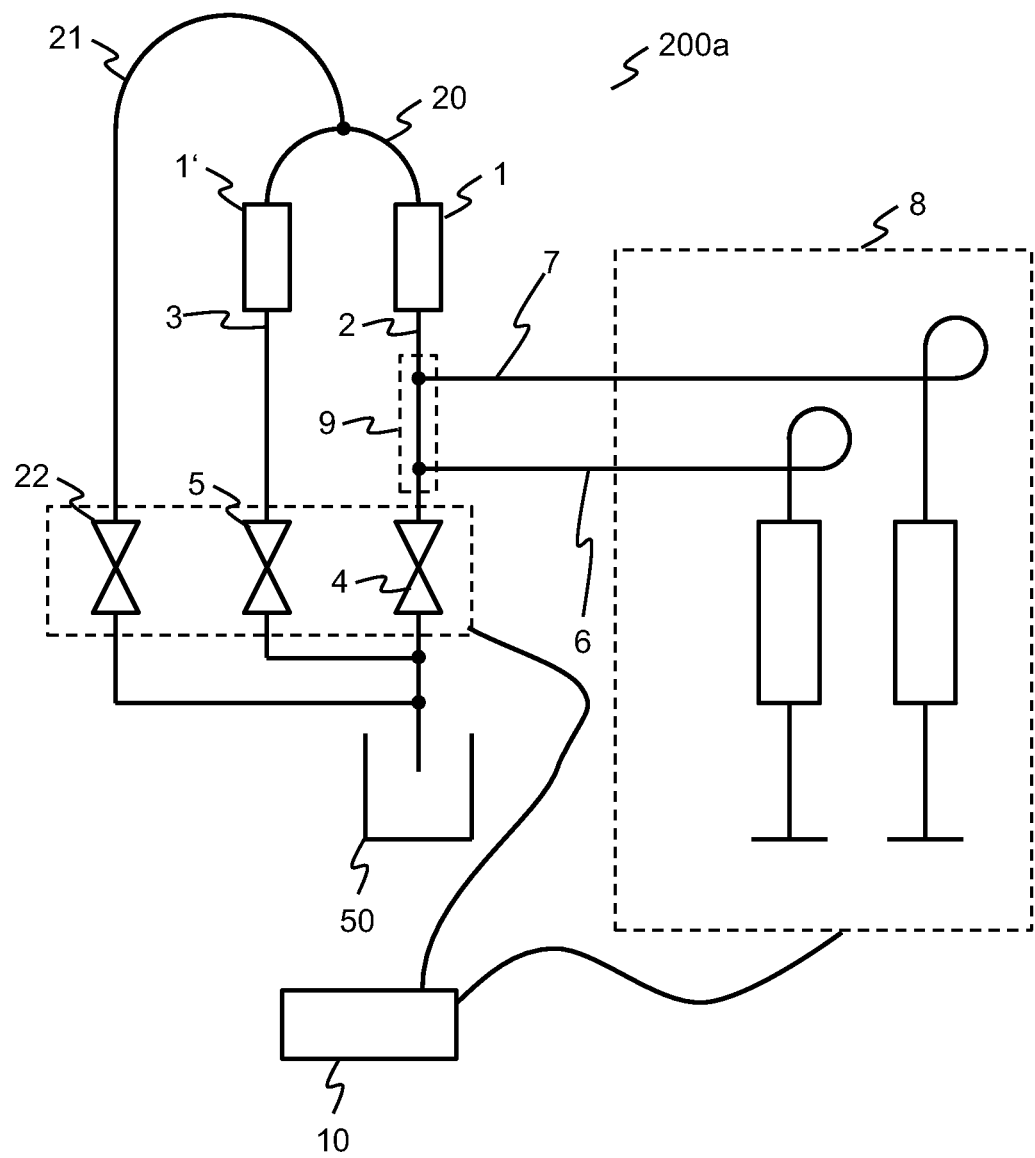
FIG. 2A Schematic view of a flow conduit system having two flow cells

FIG. 2A illustrates a schematic view of a flow conduit system (200a) having two flow cells.

Comparing to FIG. 1, the flow conduit system further comprises a second flow cell conduit (1') connected to the first flow cell conduit (1) through an intermediate conduit (20). The intermediate conduit (20) preferably has a low dead volume of below 1 microliters, in order to reduce the time differences between the measurements from the sensing areas within the first flow cell conduit (1) and the measurements from the sensing areas within the second flow cell conduit (1'). In addition, an outlet conduit (21) is operably connected to the intermediate conduit (20) by means of a second valveless junction. Using a valveless junction according to the invention, the volume of the intermediate conduit (20) can be kept low, since in general the integration of valves increases the footprint necessary for realizing the flow conduit system and thus increases the lengths and volumes of the conduits. The outlet conduit (21) has a third selector valve (22) with open and closed positions for controlling the flow within the conduit.

Using this configuration, and by controlling the corresponding switching valves and injection means (8) using the control unit (10), the fluids can be selectively either injected into the first flow cell conduit (1) only, or into the first and then the second flow cell conduit (1,1') in series, or the flow cell conduits (1,1') can be completely bypassed.

In the following, the flow paths, which are additionally possible with respect to FIG. 1, are described more in detail, (flow paths not depicted). The first fluid is allowed to flow from the second end portion of the first injection conduit (6) on the first and the second and a fifth flow path and the second fluid is allowed to flow from the second end portion of the second injection conduit (7) on the third and the fourth and a ninth flow path. The second flow path is defined by a flow from the first injection conduit (6) through the first flow cell conduit (1) and the second flow cell conduit (1') to the second end portion of the second inlet/outlet conduit (3), and the fourth flow path is defined by a flow from the second injection conduit (7) through the first flow cell conduit (1) and the second flow cell conduit (1') to the second end portion of the second inlet/outlet conduit (3). For the first, second, third and fourth flow paths, in addition to the valve configurations described for FIG. 1, the third selector valve (22) is closed. The fifth flow path is defined by a flow from the first injection conduit (6) through the first flow cell conduit (1) to the outlet conduit (21), wherein the first and second selector valves (4,5) are closed and the third selector valve (22) is opened, and the ninth flow path is defined by a flow from the second injection conduit (7) through the first flow cell conduit (1) to the outlet conduit (21), wherein the first and second selector valves (4,5) are closed and the third selector valve (22) is opened. Typically, the outlet conduit (21) is fluidly connected to a waste receptacle (50) to receive the fluids.

Typically one of the flow cell conduits (1, 1') is used as a reference flow cell, and the other one as the sensing flow cell. In this context, the reference flow cell is used to measure background fluctuations or noise, and the sensing flow cell is used to measure the actual binding of interest. The background fluctuations or noise typically originate from parasitic refractive index fluctuations within the fluids, such as due to concentration gradients or temperature fluctuations, or from non-specific adsorption of the analyte or sample to the sensor surface, or from fluctuations in the readout such as readout laser wavelength fluctuations. In this context, non-specific adsorption refers to the adsorption of analyte or sample to the sensor surface which do not occur due to the actual binding or interaction of the analyte with the ligand. Typically, the sensor signal obtained from the sensor surface within the reference flow cell is subtracted from the signal obtained within the sensing flow cell in order to at least partially eliminate the unwanted effects of background fluctuations or noise and to thereby obtain a referenced sensor signal. The subtraction is typically obtained computationally, such in a software for a computer program or within the firmware of the sensor device, or it can be obtained physically, such as in certain interferometric sensor devices where one interferometric arm is configured to read out the sensing areas within the reference flow cell and the other interferometric arm is configured to read out the sensing areas within sensing flow cell. In order to obtain a flow cell conduit which can be used as a reference flow cell, typically no ligand is immobilized or bound to the corresponding sensor surface, and the ligand is only immobilized on the sensor surface corresponding to the sensing flow cell.

The preparation and rinsing steps described for FIG. 1 in principle apply also for the arrangement in FIG. 2A. Since the second and the fourth flow paths flow through the first flow cell conduit (1) and the second flow cell conduit (1'), the measurement step described above using the second and fourth flow paths now includes contacting both flow cell conduits (1,1') in series. A further measurement step is possible using the fifth and ninth flow paths, wherein the first fluid and or the second fluid only contacts the first flow cell conduit (1) and not the second flow cell conduit (1').

Typically, for selectively immobilizing or binding a ligand on the sensor surface of the first flow cell conduit (1) in order to obtain a sensing flow cell, while not immobilizing the ligand on the sensing surface of the second flow cell conduit (1') in order to obtain a reference flow cell, the following measurement steps are executed, where the terms "is flown over both flow cell conduits (1,1')" refers to the measurement step previously described for FIG. 1 using the second and fourth flow paths, and the term "is flown over the first flow cell conduit (1)" refers to the further measurement step which is possible using the arrangement in FIG. 2A using the fifth and ninth flow paths. It is understood that each measurement step is typically preceded by a fluid preparation step and followed by a rinsing step. First, optionally, the activation fluid is used as first fluid and is flown over both flow cell conduits (1,1'), then the ligand is used as first fluid and is flown over the first flow cell conduit (1), then the passivation fluid is used as first fluid and is flown over both flow cell conduits (1,1'). Typically, for selectively immobilizing or binding a ligand on the sensor surface of the second flow cell conduit (1') in order to obtain a sensing flow cell, while not immobilizing the ligand on the sensing surface of the first flow cell conduit (1) in order to obtain a reference flow cell, the following measurement steps are executed. First, optionally, the activation fluid is used as first fluid and is flown over both flow cell conduits (1,1'), then the passivation fluid is used as first fluid and is flown over the first flow cell conduit (1) so that no ligand can bind to the sensor surface within the first flow cell conduit (1), then the ligand is used as first fluid and is flown over both flow cell conduits (1,1') so that it binds to the sensor surface within the second flow cell conduit (1') only, then the passivation fluid is used as first fluid and is flown over both flow cell conduits (1,1'). Using the inventive arrangement in FIG. 2A, it is also possible to immobilize a first ligand on the sensor surface within the first flow cell conduit (1), and to immobilize a second ligand on the sensor surface within the second flow cell conduit (1'). In order to achieve this, typically the following measurement steps are executed. First, optionally, the activation fluid is used as first fluid and is flown over both flow cell conduits (1,1'), then the first ligand is used as first fluid and is flown over the first flow cell conduit (1) so that it binds to the sensor surface within the first flow cell conduit (1) only, then the passivation fluid is used as first fluid and is flown over the first flow cell conduit (1) so that the second ligand can not bind to the sensor surface within the first flow cell conduit (1), then the second ligand is used as first fluid and is flown over both flow cell conduits (1,1') so that it binds to the sensor surface within the second flow cell conduit (1') only, then the passivation fluid is used as first fluid and is flown over both flow cell conduits (1,1').

After the corresponding reference and sensing flow cells are prepared, typically successively different concentrations of the analyte or sample to be measured are used as first fluid and flown over both flow cell conduits (1,1'), and the corresponding sensor signals for both flow cell conduits are recorded, wherein the reference sensor signal is successively or directly subtracted from the sensing signal in order to obtain the referenced sensing signal. Optionally, regeneration fluids such as NaOH can be used as first fluid for regenerating the sensor surface and are typically flown over both flow cell conduits (1,1').

Figure 2B:
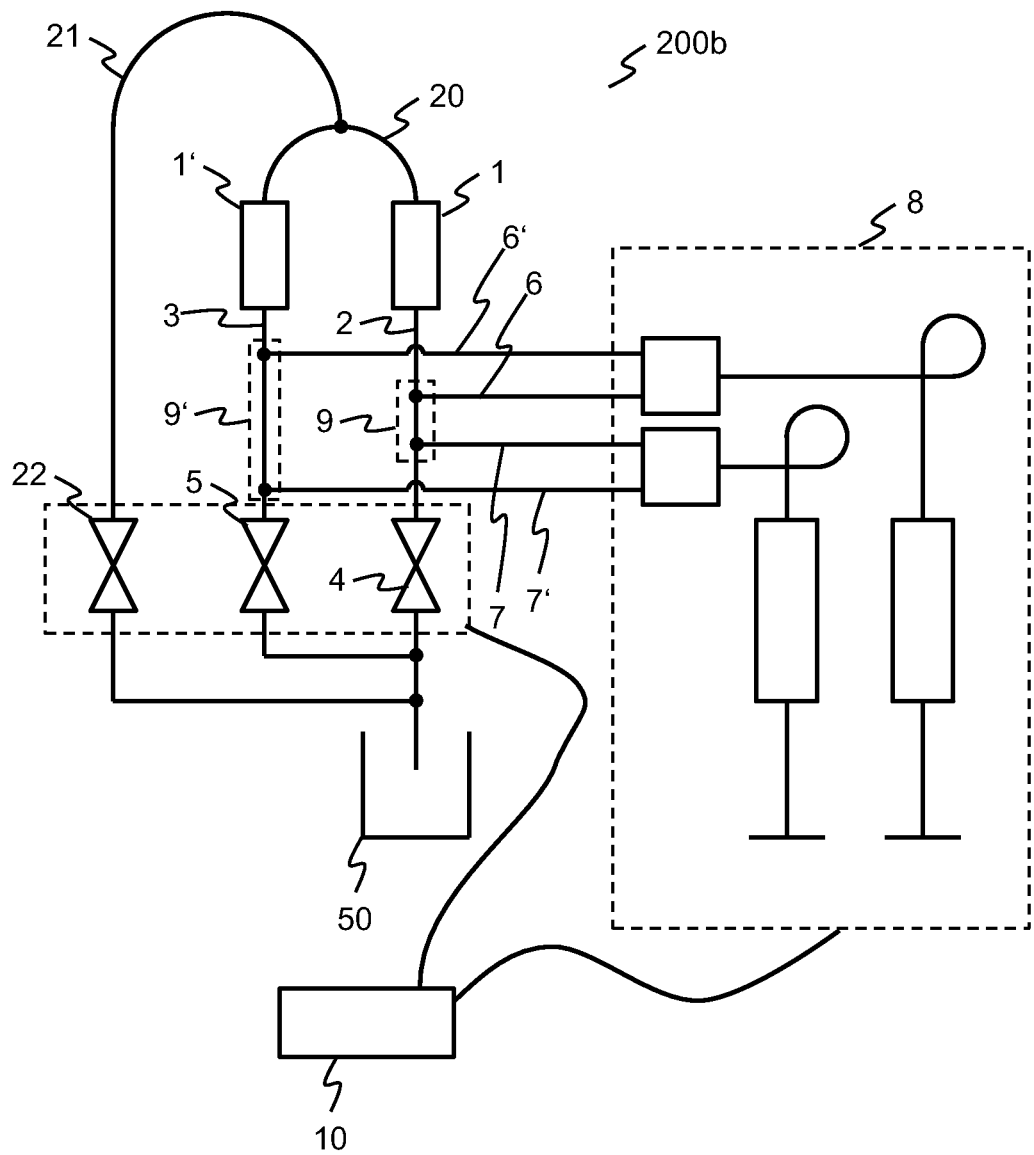
FIG. 2B Schematic view of a flow conduit system having two flow cells

FIG. 2B illustrates a schematic view of a flow conduit system (200*b*) having two flow cells.

Comparing to FIG. 1, the flow conduit system further comprises a second flow cell conduit (1') connected to the first flow cell conduit (1) through an intermediate conduit (20). The intermediate conduit (20) preferably has a low dead volume of below 1 microliters, in order to reduce the time differences between the measurements from the sensing areas within the first flow cell conduit (1) and the measurements from the sensing areas within the second flow cell conduit (1').

The flow conduit system is symmetric with respect to an imaginary line between the two flow cell conduits (1,1'). In addition, an outlet conduit (21) is operably connected to the intermediate conduit (20) by means of a second valveless junction. The outlet conduit (21) has a third selector valve (22) with open and closed positions for controlling the flow within the conduit. The injection configuration is mirrored by introducing a third injection conduit (6') and a fourth injection conduit (7') which are connected on one side by one or more third valveless junctions (9') to the second inlet/outlet conduit (3). The connection is located in between the first end portion of the second flow cell conduit (1') and the second selector valve (5). On the other side, the third and fourth injection conduits (6',7') are connected to the injecting means (8).

Using this configuration, and by controlling the corresponding selector valves (4,5,22) and injection means (8) using the control unit (10), the fluids can be selectively either injected into the first flow cell conduit (1) only, or the second flow cell conduit (1') only, or into the first and then the second flow cell conduit (1,1') in series or vice-versa, or the flow cells can be completely bypassed.

In the following, the eight flow paths, which are additionally possible with respect to FIG. 1, are described more in detail, (flow paths not depicted). The first fluid is allowed to flow from the second end portion of the first injection conduit (6) on the first and the second and a fifth flow path and from the second end portion of the third injection conduit (6') on a sixth and a seventh and an eight flow path and to allow the second fluid to flow from the second end portion of the second injection conduit (7) on the third and the fourth and a ninth flow path and from the second end portion of the fourth injection conduit (7') on a tenth and an eleventh and a twelfth flow path. There, the fifth and the ninth flow paths are defined by a flow through the first flow cell conduit (1) to the second end portion of the outlet conduit (22) without contacting the sensing areas within the second flow cell conduit (1') wherein the third selector valve (22) is opened and the first and second selector valves (4,5) are closed, and the sixth and the tenth flow paths are defined by a flow to the second end portion of the second inlet/outlet conduit (3) without contacting the sensing areas within the second or first flow cell conduits (1', 1) wherein the second selector valve (5) is opened and the first and third selector valves (4,22) are closed, and the seventh and the eleventh flow paths are defined by a flow through the second and first flow cell conduits (1', 1) to the second end portion of the first inlet/outlet conduit (2) wherein the first selector valve (4) is opened and the second and third selector valves (5,22) are closed, and the eight and twelfth flow paths are defined by a flow through the second flow cell conduit (1') to the second end portion of the outlet conduit (22) without contacting the sensing areas within the first flow cell conduit (1) wherein the third selector valve (22) is opened and the first and second selector valves (4,5) are closed.

As depicted in FIG. 2A, the configuration with two flow cell conduits (1,1') may also be realized in a non-symmetrical manner without the third and fourth injection conduits (6',7'). In this configuration, the flow cell conduits (1,1') are always contacted in the same flow direction, i.e. the sixth, seventh, eight, tenth, eleventh and twelfth flow paths are not realized with respect to the symmetrical embodiment. The non-symmetrical embodiment has the advantage that the injection means (8) can be realized without valves for selecting between first and third injection conduits (6, 6') or between second and fourth injection conduits (7, 7').

The preparation, measurement and rinsing steps described for FIG. 2A in principle apply also for the arrangement in FIG. 2B. Due to the symmetric arrangement in FIG. 2B, the possible measurement steps are multiplied, so that the flow cell conduits can also be contacted in a reverse manner by injecting through the third and fourth injection conduits (6',7'), so that first the second flow cell conduit (1') is contacted and optionally afterwards the first flow cell conduit (1), or that both flow cell conduits are bypassed. Therefore, all previously cited steps can be applied in a mirror-like fashion. The inventive arrangement in FIG. 2B has the advantage that the first and third injection conduits (6,6') used for injection of the analyte or sample can be placed closer to the corresponding flow cells (1,1') while maintaining a good definition of the fluid interface after the fluid preparation step. This can be achieved by applying a counter flow through the system as last rinsing step, i.e. by injecting neutral buffer solution through the fourth injection conduit (7') on the eleventh flow path when preparing the sample at the first valveless junction (9), or by injecting neutral buffer solution through the second injection conduit (7) on the fourth flow path when preparing the sample at the second valveless junction (9'). Furthermore, this arrangement has the advantage that a ligand can selectively be immobilized on the sensing surface within the second flow cell conduit (1') without any intermediate passivation steps. For achieving this, the following steps are executed, where the terms "is flown over both flow cell conduits (1,1')" refers to the corresponding measurement step previously described for FIG. 1, and the term "is flown over the second flow cell conduit (1')" refers to a further measurement step which is possible using the arrangement in FIG. 2B using the eight and twelfth flow paths. It is understood that each measurement step is typically preceded by a fluid preparation step and followed by a rinsing step. First, optionally, the activation fluid is used as first fluid and is flown over both flow cell conduits (1,1'), then the ligand is used as first fluid and is flown over the second flow cell conduit (1'), then the passivation fluid is used as first fluid and is flown over both flow cell conduits (1,1').

After the corresponding reference and sensing flow cells are prepared, typically successively different concentrations of the analyte or sample to be measured are used as first fluid and flown over both flow cell conduits (1,1') in one direction or the other, i.e. first over the first flow cell conduit (1) and then over the second flow cell conduit (1'), or first over the second flow cell conduit (1') and then over the first flow cell conduit (1), and the corresponding sensor signals for both flow cell conduits are recorded, wherein the reference sensor signal is successively or directly subtracted from the sensing signal in order to obtain the referenced sensing signal. Optionally, regeneration fluids such as NaOH can be used as first fluid for regenerating the sensor surface and are typically flown over both flow cell conduits (1,1') in the same direction as used for the analyte or sample flow.

Figure 3:
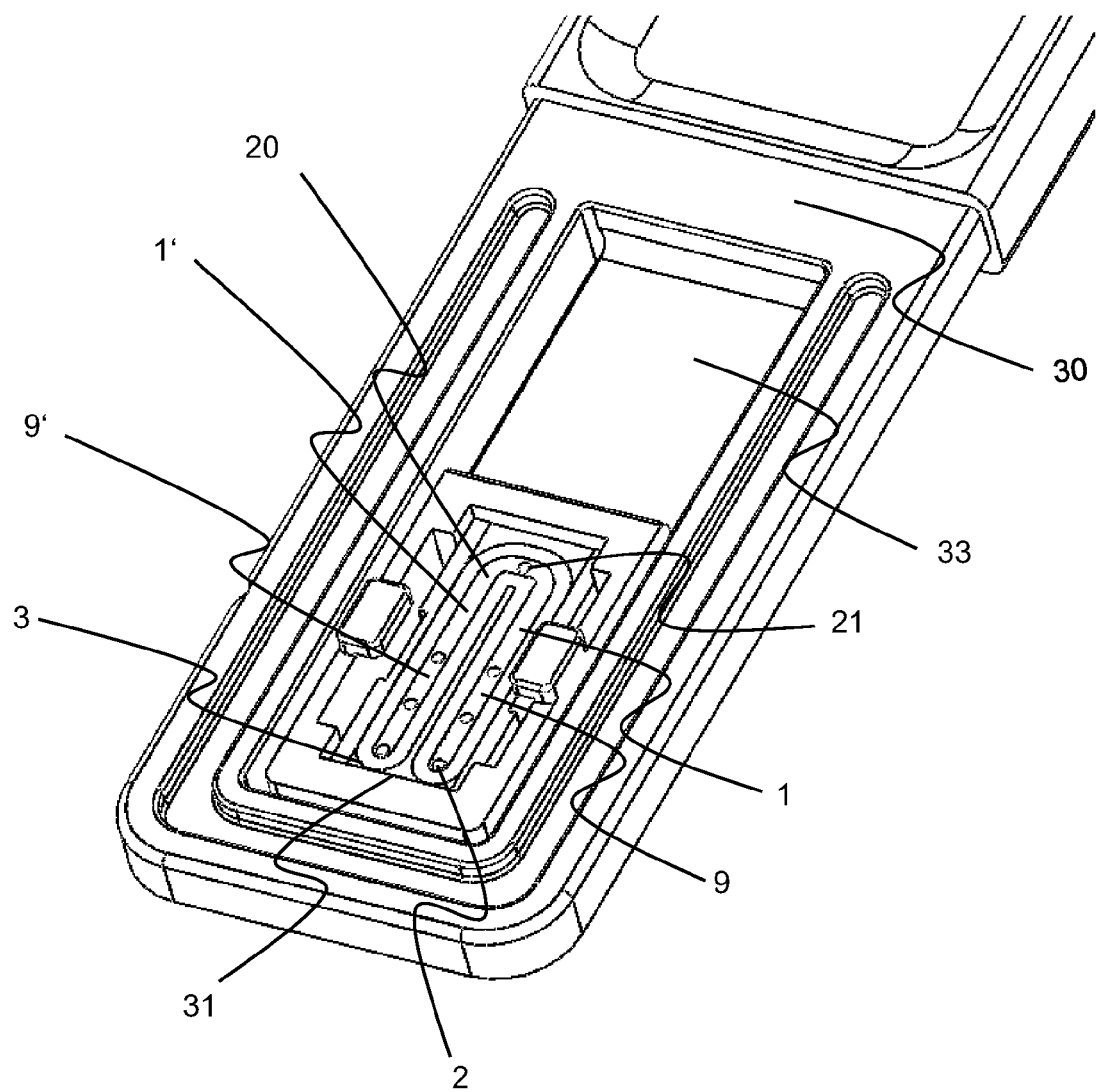
FIG. 3 Perspective view of a component for a cartridge including a removable part of a flow conduit system The reference marks utilized in the drawings and their significance is summarized in the list of reference marks. Principally in the figures the same parts are identified with the same reference marks.

FIG. 3 illustrates the perspective view of a component for a cartridge including a removable part of a flow conduit system (31). The component for a cartridge is preferably but not limited to an injection molded part of a relatively stiff and biocompatible or bioinert material such as PEEK or Cyclic Olefin Copolymer (COC) or Cyclic Olefin Polymer (COP), in which typically a sensor chip can be mounted which comprises the sensing areas and being adapted to provide a sensor signal using an appropriate readout unit. The removable part of a flow conduit system comprises part of a flow conduit system as shown in FIG. 2B. The removable part of a flow conduit system comprises the first and second flow cell conduits (1,1'), the intermediate conduit (20), the outlet (21) as an output port, part of first and second inlet/outlet conduits (2,3) including corresponding output ports, and the valveless junctions (9,9') each including two inlet ports. The corresponding conduits are formed by the depicted component for a cartridge, the sensor chip (not shown), and sealing components (not shown) which define the side walls of the conduits and which are preferably formed from an elastomer material such as EPDM.

The depicted component for a cartridge includes a positioning cantilever (33) or flexure beam, which allows the positioning of the removable part of the flow conduit system (31) and thus the sensing areas in a direction at least close to perpendicular to the chip. The positioning cantilever (33) is preferably integrally formed into the component for a cartridge, and fixed at one end at the structure containing the removable part of the flow conduits, and on the other end at a frame of the component for a cartridge. The advantage of such a flexible positioning of the removable part of the flow conduits and sensing areas areas in a direction at least close to perpendicular to the chip is that a precise positioning in that direction can be achieved by using a corresponding clamping force. The precise positioning allows for a reliable readout in case of optical readout schemes such as SPR or waveguide-based sensors, and on the other hand allows for a reliable fluidic connection without leaks between the fixed part and the removable part of the flow conduit system (31). A clamping mechanism on a receiving part, such as a docking station (not shown) of the biochemical sensor, can thus position the sensor chip and removable part of the flow conduit system (31) and hold it in a fixed position during the measurement by applying a certain force on the side opposite to the sensor chip, typically thereby pressing it against a receiving surface, without being affected by thermal dilation effects typically occurring within the cartridge which preferably is a plastic injection molded part. Preferably, the clamping mechanism comprises a fluidic interface part movable in the direction of the clamping force and comprising a portion of the injection conduits (6,7,6',7') and the outlet conduit (21), which is operably connected a manual lever or motor to activate the clamping through a screw mechanism. Preferably, such a lever is connected to a hatch which is opened and closed in order to insert the cartridge, such as no clamping force is applied onto the cartridge when the hatch is open so that the cartridge can be removed, and such as a clamping force is applied when the hatch is closed so that the cartridge is secured and the fluidic connections are reliably established between the fixed part and the removable part of the flow conduit system (31). Typically, the fluidic connection between the removable part of the fluidic system (31) and the fluidic interface part on the fixed part of the fluidic system is realized using elastomeric seals such as miniature O-rings, which are compressed upon activation of the clamping mechanism and thus make a sealed connection between the flow conduits of the removable part of the fluidic system (31) and the fixed part of the fluidic system.

LIST OF REFERENCE MARKS

1 First flow cell conduit
1' Second flow cell conduit
2 First inlet/outlet conduit
3 Second inlet/outlet conduit
4 First selector valve
5 Second selector valve
6 First injection conduit
7 Second injection conduit
8 Injecting means
9 First valveless junctions
10 Control unit
20 Intermediate conduit
21 Outlet conduit
22 Third selector valve
30 Cartridge
31 Removable part of the flow conduit system
33 Positioning cantilever
50 Waste receptacle
100 Flow conduit system
200a Flow conduit system
200b Flow conduit system

The invention claimed is:

1. A flow conduit system suitable for biochemical sensing, the flow conduit system comprising,
   a first flow cell conduit comprising one or more sensing areas for biochemical sensing;
   a second flow cell conduit which comprises one or more sensing areas for biochemical sensing, which is fluidly connected to the first flow cell conduit;
   a first selector valve;
   a second selector valve which is fluidly connected to the first flow cell conduit;
   a first inlet/outlet conduit which has a first end which is connected to the first flow cell conduit and a second end which is connected to the first selector valve, so as to fluidly connect the first flow cell conduit to the first selector valve;
   a first injection conduit having a first end and a second end;
   a second injection conduit having a first end and a second end;
   a fluid injecting means fluidly connected to the second ends of each of the first and second injection conduits so that the fluid injecting means can selectively inject fluids into the first and/or second injection conduits;
   a control unit for controlling the fluid injection means and the first and second selector valves;
   wherein the first injection conduit is fluidly connected, at its first end, to the first inlet/outlet conduit by a valveless junction, and the second injection conduits is fluidly connected, at its first end, to the first inlet/outlet conduit by a valveless junction,
   wherein the control unit is configured to consecutively,
   (i) open the first selector valve and close the second selector valve, and to then initiate the injecting means to inject a sample fluid which contains molecules to be sensed into the first injection conduit, so that the sample fluid flows through the first injection conduit and to the first selector valve without passing through the first flow cell conduit; and, (ii) close the first selector valve and open the second selector valve, and to then initiate the injecting means to inject a sample fluid, which contains molecules to be sensed, into the first injection conduit, so that the sample fluid flows through the first injection conduit and through the first flow cell conduit to the second selector valve.

2. A flow conduit system suitable for biochemical sensing, the flow conduit system comprising,
a first flow cell conduit comprising one or more sensing areas for biochemical sensing;
a first selector valve;
a second selector valve which is fluidly connected to the first flow cell conduit;
a first inlet/outlet conduit which has a first end which is connected to the first flow cell conduit and a second end which is connected to the first selector valve, so as to fluidly connect the first flow cell conduit to the first selector valve;
a first injection conduit having a first end and a second end;
a second injection conduit having a first end and a second end;
a fluid injecting means fluidly connected to the second ends of each of the first and second injection conduits so that the fluid injecting means can selectively inject fluids into the first and/or second injection conduits;
a control unit for controlling the fluid injection means and the first and second selector valves;
wherein the first injection conduit is fluidly connected, at its first end, to the first inlet/outlet conduit by a valveless junction, and the second injection conduits is fluidly connected, at its first end, to the first inlet/outlet conduit by a valveless junction,
wherein the control unit is configured to consecutively,
(i) open the first selector valve and close the second selector valve, and to then initiate the injecting means to inject a sample fluid which contains molecules to be sensed into the first injection conduit, so that the sample fluid flows through the first injection conduit and to the first selector valve without passing through the first flow cell conduit; and,
(ii) close the first selector valve and open the second selector valve, and to then initiate the injecting means to inject a sample fluid, which contains molecules to be sensed, into the first injection conduit, so that the sample fluid flows through the first injection conduit and through the first flow cell conduit to the second selector valve,
wherein the control unit is configured to carry out said steps of, (i) open the first selector valve and close the second selector valve, and to then initiate the injecting means to inject a sample fluid which contains molecules to be sensed into the first injection conduit, so that the sample fluid flows through the first injection conduit and to the first selector valve without passing through the first flow cell conduit, before carrying out the steps of, (ii) close the first selector valve and open the second selector valve, and to then initiate the injecting means to inject a sample fluid, which contains molecules to be sensed, into the first injection conduit, so that the sample fluid flows through the first injection conduit and through the first flow cell conduit to the second selector valve.

3. A flow conduit system according to claim 2, wherein the first injection conduit and the second injection conduit are each valveless and wherein the portion of the first inlet/outlet conduit which is between the first flow cell conduit and valveless junction is valveless.

4. A flow conduit system according to claim 2, wherein the fluid injecting means comprises a means by which the volume of fluid which is injected from the fluid injecting means into the first and/or second injection conduits can be controlled.

5. A flow conduit system according to claim 2, wherein the fluid injecting means comprises a means by which the rate at which fluid is injected from the fluid injecting means into the first and/or second injection conduits can be controlled.

6. A flow conduit system according to claim 2, wherein the volume of the first inlet/outlet conduit which is between the first flow cell conduit and a valveless junction is less than 10 microliters.

7. A flow conduit system according to claim 2, wherein the control unit is configured to control the fluid injection means such that the volume of fluid which is injected from the fluid injecting means into the first and/or second injection conduits, and the rate at which fluid is injected from the fluid injecting means into the first and/or second injection conduits, is automatically controlled.

8. A flow conduit system according to claim 2, wherein the flow conduit system further comprises a second flow cell conduit which comprises one or more sensing areas for biochemical sensing, which is fluidly connected to the first flow cell conduit.

9. A flow conduit system according to claim 8, wherein the flow conduit system further comprises a second inlet/outlet conduit fluidly connected to the second flow cell conduit; and wherein the second inlet/outlet conduit fluidly connects the second flow cell conduit to the second selector valve.

10. A flow conduit system according to claim 8, wherein the flow conduit system further comprises,
a third injection conduit having a first end and a second end;
a fourth injection conduit having a first end and a second end;
and wherein the fluid injecting means is further fluidly connected to the second ends of each of the third and fourth injection conduits so that the fluid injecting means can selectively inject fluids into the third and/or fourth injection conduits, and
wherein the third injection conduit is fluidly connected, at its first end, to the second inlet/outlet conduit by a valveless junction, and the fourth injection conduit is fluidly connected, at its first end, to the second inlet/outlet conduit by a valveless junction.

11. A flow conduit system according to claim 2, wherein the valveless junction and the first flow cell conduit are all provided on a single cartridge and wherein the single cartridge comprises a fixed portion and a flexible cantilever which is attached to the fixed portion at one end and which has a free end which can be flexed to move relative to the fixed portion, wherein the valveless junction, and first flow cell conduit are provided on the flexible cantilever and wherein the single cartridge comprises connecting means which are configured to allow the single cartridge to be removeably attached to the flow conduit system, so that the valveless junction and first flow cell conduit can be selectively removed from the flow conduit system.

12. A method for performing biochemical sensing, using a flow conduit system which comprises
a first flow cell conduit comprising one or more sensing areas for biochemical sensing;

a first selector valve;
a second selector valve which is fluidly connected to the first flow cell conduit;
a first inlet/outlet conduit which has a first end which is connected to the first flow cell conduit and a second end which is connected to the first selector valve, so as to fluidly connect the first flow cell conduit to the first selector valve;
a first injection conduit having a first end and a second end;
a second injection conduit having a first end and a second end;
a fluid injecting means fluidly connected to the second ends of each of the first and second injection conduits so that the fluid injecting means can selectively inject fluids into the first and/or second injection conduits;
a control unit for controlling the fluid injection means and the first and second selector valves;
wherein the first injection conduit is fluidly connected, at its first end, to the first inlet/outlet conduit by a valveless junction, and the second injection conduits is fluidly connected, at its first end, to the first inlet/outlet conduit by a valveless junction,
wherein the control unit is configured to consecutively,
(i) open the first selector valve and close the second selector valve, and to then initiate the injecting means to inject a sample fluid which contains molecules to be sensed into the first injection conduit, so that the sample fluid flows through the first injection conduit and to the first selector valve without passing through the first flow cell conduit; and,
(ii) close the first selector valve and open the second selector valve, and to then initiate the injecting means to inject a sample fluid, which contains molecules to be sensed, into the first injection conduit, so that the sample fluid flows through the first injection conduit and through the first flow cell conduit to the second selector valve,
wherein the control unit is configured to carry out said steps of, (i) open the first selector valve and close the second selector valve, and to then initiate the injecting means to inject a sample fluid which contains molecules to be sensed into the first injection conduit, so that the sample fluid flows through the first injection conduit and to the first selector valve without passing through the first flow cell conduit, before carrying out the steps of, (ii) close the first selector valve and open the second selector valve, and to then initiate the injecting means to inject a sample fluid, which contains molecules to be sensed, into the first injection conduit, so that the sample fluid flows through the first injection conduit and through the first flow cell conduit to the second selector valve;
the method comprising the steps of,
(a) filling the flow conduit system with buffer fluid;
(b) opening the first selector valve, and closing the second selector valve;
(c) using the injecting means to inject a sample fluid which contains molecules to be sensed, into the first injection conduit so that the sample fluid flows through the first injection conduit and to the first selector valve;
(d) using the injection means to inject buffer fluid into the second injection conduit and flowing the buffer fluid along the second injection conduit, into the first inlet/outlet conduit, and through the first selector valve;
(e) stopping the injection means from injecting the buffer fluid;
(f) using said buffer fluid to restrict the flow of the sample fluid from the first injection conduit into the first inlet/outlet conduit;
(g) closing the first selector valve and opening the second selector valve;
(h) using the injection means to inject more sample fluid which contains molecules to be sensed, into the first injection conduit, so that the sample fluid flows through the first flow cell conduit;
(i) using the first flow cell conduit to sense the amount of said molecules to be sensed which have bound to sensing areas of the first flow cell conduit.

13. A method of claim 12 for performing biochemical sensing, using a flow conduit system which comprises,
a first flow cell conduit comprising one or more sensing areas for biochemical sensing;
a second flow cell conduit which comprises one or more sensing areas for biochemical sensing, which is fluidly connected to the first flow cell conduit;
a first selector valve;
a second selector valve which is fluidly connected to the first flow cell conduit;
a first inlet/outlet conduit which has a first end which is connected to the first flow cell conduit and a second end which is connected to the first selector valve so as to fluidly connect the first flow cell conduit to the first selector valve;
a first injection conduit having a first end and a second end;
a second injection conduit having a first end and a second end;
a fluid injecting means fluidly connected to the second ends of each of the first and second injection conduits so that the fluid injecting means can selectively inject fluids into the first and/or second injection conduits;
a control unit for controlling the fluid injection means and the first and second selector valves;
wherein the first injection conduit is fluidly connected, at its first end, to the first inlet/outlet conduit by a valveless junction, and the second injection conduits is fluidly connected, at its first end, to the first inlet/outlet conduit by a valveless junction,
wherein the control unit is configured to consecutively,
(i) open the first selector valve and close the second selector valve, and to then initiate the injecting means to inject a sample fluid which contains molecules to be sensed into the first injection conduit, so that the sample fluid flows through the first injection conduit and to the first selector valve without passing through the first flow cell conduit; and,
(ii) close the first selector valve and open the second selector valve, and to then initiate the injecting means to inject a sample fluid, which contains molecules to be sensed, into the first injection conduit, so that the sample fluid flows through the first injection conduit and through the first flow cell conduit to the second selector valve,
wherein the control unit is configured to carry out said steps of, (i) open the first selector valve and close the second selector valve, and to then initiate the injecting means to inject a sample fluid which contains molecules to be sensed into the first injection conduit, so that the sample fluid flows through the first injection conduit and to the first selector valve without passing through the first flow cell conduit, before carrying out the steps of, (ii) close the first selector valve and open the second selector valve, and to then initiate the injecting means to inject a sample fluid, which contains molecules to be sensed, into the first injection conduit, so that the sample fluid flows through the first injection conduit and through the first flow cell conduit to the second selector valve, the method comprising the steps of,
(a) performing the steps (a)-(h) of the method of claim 12;
(b) sensing background fluctuations in the sample as the sample is flowing through the first flow cell conduit
(c) outputting a signal from the first flow cell conduit which is indicative of the background fluctuations in the sample;
(d) flowing the sample through the second flow cell conduit;
(e) sensing the amount of said molecules to be sensed which have bound to sensing areas of the second flow cell conduit as the sample is flowing through the second flow cell conduit;
(f) outputting a signal from the second flow cell conduit which is indicative of the amount of molecules to be sensed which have bound to sensing areas of the second flow cell conduit;
(g) subtracting the signal output by the first flow cell conduit from the signal output be the second flow cell conduit.

14. A method for performing biochemical sensing, using a flow conduit system which comprises
a first flow cell conduit comprising one or more sensing areas for biochemical sensing;
a second flow cell conduit which comprises one or more sensing areas for biochemical sensing, which is fluidly connected to the first flow cell conduit;
a first selector valve;
a second selector valve which is fluidly connected to the first flow cell conduit;
a first inlet/outlet conduit which has a first end which is connected to the first flow cell conduit and a second end which is connected to the first selector valve, so as to fluidly connect the first flow cell conduit to the first selector valve;
a first injection conduit having a first end and a second end;
a second injection conduit having a first end and a second end;
a fluid injecting means fluidly connected to the second ends of each of the first and second injection conduits so that the fluid injecting means can selectively inject fluids into the first and/or second injection conduits;
a control unit for controlling the fluid injection means and the first and second selector valves;
wherein the first injection conduit is fluidly connected, at its first end, to the first inlet/outlet conduit by a valveless junction, and the second injection conduits is fluidly connected, at its first end, to the first inlet/outlet conduit by a valveless junction;
a third injection conduit having a first end and a second end;
a fourth injection conduit having a first end and a second end;
and wherein the fluid injecting means is further fluidly connected to the second ends of each of the third and fourth injection conduits so that the fluid injecting means can selectively inject fluids into the third and/or fourth injection conduits, and wherein the third injection conduit is fluidly connected, at its first end, to the second inlet/outlet conduit by a valveless junction, and the fourth injection conduit is fluidly connected, at its first end, to the second inlet/outlet conduit by a valveless junction;
wherein the control unit is configured to consecutively,
(i) open the first selector valve and close the second selector valve, and to then initiate the injecting means to inject a sample fluid which contains molecules to be sensed into the first injection conduit, so that the sample fluid flows through the first injection conduit and to the first selector valve without passing through the first flow cell conduit; and,
(ii) close the first selector valve and open the second selector valve, and to then initiate the injecting means to inject a sample fluid, which contains molecules to be sensed, into the first injection conduit, so that the sample fluid flows through the first injection conduit and through the first flow cell conduit to the second selector valve,
wherein the control unit is configured to carry out said steps of, (i) open the first selector valve and close the second selector valve, and to then initiate the injecting means to inject a sample fluid which contains molecules to be sensed into the first injection conduit, so that the sample fluid flows through the first injection conduit and to the first selector valve without passing through the first flow cell conduit, before carrying out the steps of, (ii) close the first selector valve and open the second selector valve, and to then initiate the injecting means to inject a sample fluid, which contains molecules to be sensed, into the first injection conduit, so that the sample fluid flows through the first injection conduit and through the first flow cell conduit to the second selector valve;
the method comprising the steps of,
(a) filling the flow conduit system with buffer fluid;
(b) opening the first selector valve;
(c) using the injecting means to inject a sample fluid which contains molecules to be sensed, into the injection conduit whose first end is connected to the first inlet/outlet conduit by a first valveless junction which is located closest to the first flow cell conduit;
(d) using said buffer fluid to restrict the flow of the sample fluid from the said injection conduit into the first inlet/outlet conduit;
(e) using the injection means to inject buffer fluid into either the third or fourth injection conduit and flowing the buffer fluid along the second inlet/outlet conduit, through the second flow cell conduit, through the first flow cell conduit and through the selector valve;
(f) stopping the injection means from injecting the buffer fluid;
(g) closing the first selector valve;
(h) using the injection means to inject more sample fluid which contains molecules to be sensed, into said injection conduit used in step (c) so that the sample fluid flows into the first flow cell conduit via the valveless junction which is located closest to the first flow cell conduit;
(i) using the first flow cell conduit to sense the amount of said molecules to be sensed which have bound to sensing areas of the first flow cell conduit.

* * * * *